US011992222B2

(12) United States Patent
Shellenberger et al.

(10) Patent No.: US 11,992,222 B2
(45) Date of Patent: May 28, 2024

(54) SURGICAL CLIP

(71) Applicant: TELEFLEX MEDICAL INCORPORATED, Morrisville, NC (US)

(72) Inventors: Carson Shellenberger, Cary, NC (US); Ian Enniss, Morrisville, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 246 days.

(21) Appl. No.: 17/127,973

(22) Filed: Dec. 18, 2020

(65) Prior Publication Data
US 2021/0186511 A1 Jun. 24, 2021

Related U.S. Application Data

(60) Provisional application No. 62/950,819, filed on Dec. 19, 2019.

(51) Int. Cl.
*A61B 17/122* (2006.01)

(52) U.S. Cl.
CPC .................................. *A61B 17/122* (2013.01)

(58) Field of Classification Search
CPC . A61B 17/122; A61B 17/1227; A61B 17/128; A61B 17/1285; A61B 17/10; A61B 17/08; A61B 17/083; A61B 17/12; A61B 2017/1225; A61M 39/284; F61K 7/063
USPC .................................................. 606/152, 120
See application file for complete search history.

(56) References Cited

U.S. PATENT DOCUMENTS

| 1,728,322 | A | 9/1929 | Badrian |
| 2,384,697 | A | 9/1945 | Riccardi |
| 2,498,372 | A | 2/1950 | Kortlucke et al. |
| 2,598,901 | A | 6/1952 | Garland |
| 2,626,608 | A | 1/1953 | Garland |

(Continued)

FOREIGN PATENT DOCUMENTS

| CN | 101507646 A | 8/2009 |
| CN | 101543418 A | 9/2009 |

(Continued)

OTHER PUBLICATIONS

International Search Report and Written Opinion issued in PCT/US2020/066178, dated Apr. 6, 2021.

(Continued)

*Primary Examiner* — Tan-Uyen T Ho
*Assistant Examiner* — Bridget E. Rabaglia
(74) *Attorney, Agent, or Firm* — BakerHostetler

(57) ABSTRACT

A surgical clip may include a first leg member having a first inner surface with a curvature, the first leg member having a first thickness in a vertical direction, a first width in a lateral direction, and a first length in a longitudinal direction, where the first width is greater than the first thickness along at least half of the first length. The surgical clip may also include a second leg member having a second inner surface with a curvature, the second leg member having a plurality of teeth. The first width may be defined by first and second lateral protrusion extending from opposing side surfaces of the first leg member. The first width may be greater than a second width of an inner portion of the first leg member and a third width of an outer portion of the first leg member.

19 Claims, 9 Drawing Sheets

(56) References Cited

U.S. PATENT DOCUMENTS

| | | |
|---|---|---|
| 2,635,238 A | 4/1953 | Garland |
| 3,171,184 A | 3/1965 | Lage |
| 3,503,397 A | 3/1970 | Fogarty et al. |
| 3,766,925 A | 10/1973 | Rubricius |
| 3,825,012 A | 7/1974 | Nicoll |
| 3,867,944 A | 2/1975 | Samuels |
| 3,874,042 A | 4/1975 | Eddleman et al. |
| 3,924,629 A | 12/1975 | Akiyama |
| 4,212,303 A | 7/1980 | Nolan |
| 4,227,730 A | 10/1980 | Alexander et al. |
| 4,337,774 A | 7/1982 | Perlin |
| 4,340,061 A | 7/1982 | Kees et al. |
| 4,345,600 A | 8/1982 | Rothfuss |
| 4,346,869 A | 8/1982 | MacNeill |
| 4,390,019 A | 6/1983 | LeVeen et al. |
| 4,418,694 A | 12/1983 | Beroff et al. |
| 4,434,795 A | 3/1984 | Mericle |
| 4,449,531 A | 5/1984 | Cerwin et al. |
| 4,450,840 A | 5/1984 | Mericle et al. |
| 4,458,682 A | 7/1984 | Cerwin |
| 4,476,865 A | 10/1984 | Failla et al. |
| 4,487,205 A | 12/1984 | Di et al. |
| 4,519,392 A | 5/1985 | Lingua |
| 4,527,562 A | 7/1985 | Mericle |
| 4,550,729 A | 11/1985 | Cerwin et al. |
| 4,558,699 A | 12/1985 | Bashour |
| 4,579,118 A | 4/1986 | Failla |
| 4,588,160 A | 5/1986 | Flynn et al. |
| 4,589,626 A | 5/1986 | Kurtz et al. |
| 4,638,804 A | 1/1987 | Jewusiak |
| 4,667,671 A | 5/1987 | Danzig |
| 4,673,161 A | 6/1987 | Flynn et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,096 A | 5/1989 | Oh et al. |
| 4,844,066 A | 7/1989 | Stein |
| 4,870,965 A | 10/1989 | Jahanger |
| 4,936,447 A | 6/1990 | Peiffer |
| 4,938,215 A | 7/1990 | Schulman et al. |
| 4,938,765 A | 7/1990 | Rasmusson |
| 4,942,886 A | 7/1990 | Timmons |
| 4,950,275 A | 8/1990 | Donini |
| 4,955,897 A | 9/1990 | Ship |
| 4,961,499 A | 10/1990 | Kulp |
| 4,972,949 A | 11/1990 | Peiffer |
| 4,976,722 A * | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,160,339 A | 11/1992 | Chen et al. |
| 5,171,251 A | 12/1992 | Bregen et al. |
| 5,171,252 A | 12/1992 | Friedland |
| 5,171,253 A | 12/1992 | Klieman |
| 5,201,416 A | 4/1993 | Taylor |
| 5,222,961 A | 6/1993 | Nakao et al. |
| 5,234,449 A | 8/1993 | Bruker et al. |
| 5,242,456 A | 9/1993 | Nash et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,366,459 A | 11/1994 | Yoon |
| 5,376,101 A | 12/1994 | Green et al. |
| 5,395,381 A | 3/1995 | Green et al. |
| 5,441,509 A | 8/1995 | Vidal et al. |
| 5,462,555 A | 10/1995 | Bolanos et al. |
| 5,474,572 A | 12/1995 | Hayhurst |
| 5,474,732 A | 12/1995 | Korthoff et al. |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,575,802 A | 11/1996 | McQuilkin et al. |
| 5,626,592 A | 5/1997 | Phillips et al. |
| 5,667,516 A | 9/1997 | Allen |
| 5,676,676 A | 10/1997 | Porter |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,810,853 A | 9/1998 | Yoon |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,947,980 A | 9/1999 | Jensen et al. |
| 5,997,548 A | 12/1999 | Jahanger |
| 6,015,417 A | 1/2000 | Reynolds, Jr. |
| RE36,720 E | 5/2000 | Green et al. |
| 6,099,539 A | 8/2000 | Howell et al. |
| 6,131,576 A | 10/2000 | Davis |
| 6,206,896 B1 | 3/2001 | Howell et al. |
| 6,210,419 B1 | 4/2001 | Mayenberger et al. |
| 6,217,590 B1 | 4/2001 | Levinson |
| 6,261,303 B1 | 7/2001 | Mayenberger et al. |
| 6,273,903 B1 | 8/2001 | Wilk |
| 6,305,387 B1 | 10/2001 | Atchison |
| 6,312,445 B1 | 11/2001 | Fogarty et al. |
| 6,348,057 B1 | 2/2002 | Porat |
| 6,349,727 B1 | 2/2002 | Stewart, Jr. |
| 6,387,106 B1 | 5/2002 | Howell et al. |
| 6,391,035 B1 | 5/2002 | Appleby et al. |
| 6,419,682 B1 | 7/2002 | Appleby et al. |
| 6,461,368 B2 | 10/2002 | Fogarty et al. |
| 6,485,503 B2 | 11/2002 | Jacobs et al. |
| 6,537,289 B1 | 3/2003 | Kayan et al. |
| 6,638,282 B2 | 10/2003 | Ramsey et al. |
| 6,699,258 B1 | 3/2004 | Sadler et al. |
| 6,719,766 B1 | 4/2004 | Buelna et al. |
| 6,780,195 B2 | 8/2004 | Porat |
| 6,824,547 B2 | 11/2004 | Wilson et al. |
| 6,843,253 B2 | 1/2005 | Parkes |
| 6,863,675 B2 | 3/2005 | Wilson, Jr. |
| 6,880,699 B2 | 4/2005 | Gallagher |
| 6,989,017 B2 | 1/2006 | Howell et al. |
| 7,001,412 B2 | 2/2006 | Gallagher et al. |
| 7,052,504 B2 | 5/2006 | Hughett |
| 7,107,995 B2 | 9/2006 | Parkes |
| 7,131,977 B2 | 11/2006 | Fowler |
| 7,211,091 B2 | 5/2007 | Fowler et al. |
| 7,211,092 B2 | 5/2007 | Hughett |
| 7,316,696 B2 | 1/2008 | Wilson et al. |
| 7,326,223 B2 | 2/2008 | Wilson, Jr. |
| 7,329,266 B2 | 2/2008 | Royse et al. |
| 7,402,164 B2 | 7/2008 | Watson et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,892,244 B2 | 2/2011 | Monassevitch et al. |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,262,639 B2 | 9/2012 | Mathias |
| 8,465,507 B2 | 6/2013 | Cosgrove et al. |
| 8,517,970 B2 | 8/2013 | Mathias et al. |
| 8,795,302 B2 | 8/2014 | Wild |
| 8,945,151 B2 | 2/2015 | Salas |
| 8,945,157 B2 | 2/2015 | Gordon et al. |
| 9,084,596 B2 | 7/2015 | Stanley et al. |
| 9,119,627 B2 | 9/2015 | Cosgrove et al. |
| 9,220,507 B1 | 12/2015 | Patel et al. |

(56) References Cited

U.S. PATENT DOCUMENTS

| | | |
|---|---|---|
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,855,053 B2 | 1/2018 | Bagaoisan et al. |
| 9,901,352 B2 | 2/2018 | Fago et al. |
| 10,130,373 B2 | 11/2018 | Castro et al. |
| 10,136,898 B2 | 11/2018 | Schmidt et al. |
| 10,201,353 B2 | 2/2019 | Menn |
| 10,258,345 B2 | 4/2019 | Brown |
| 10,265,079 B2 | 4/2019 | Brodaczewski et al. |
| 10,285,712 B2 | 5/2019 | Cosgrove et al. |
| 10,307,166 B2 | 6/2019 | Willett et al. |
| 10,327,762 B2 | 6/2019 | Lear |
| 10,335,157 B2 | 7/2019 | Patel et al. |
| 10,383,637 B2 | 8/2019 | Castro |
| 10,384,049 B2 | 8/2019 | Stanton et al. |
| 10,426,488 B2 | 10/2019 | Michler et al. |
| 10,542,998 B2 | 1/2020 | Whiting |
| 10,548,609 B2 | 2/2020 | Ramsey et al. |
| 10,687,822 B2 | 6/2020 | Bachar |
| 10,722,235 B2 | 7/2020 | Baril et al. |
| 10,729,448 B2 | 8/2020 | Patel et al. |
| 10,758,243 B2 | 9/2020 | Salas |
| 10,820,909 B2 | 11/2020 | Bagaoisan et al. |
| 10,881,414 B2 | 1/2021 | Lebens, III |
| 10,925,616 B2 | 2/2021 | Shellenberger et al. |
| 10,932,788 B2 | 3/2021 | Thomas et al. |
| 10,932,789 B2 | 3/2021 | Thomas et al. |
| 10,945,740 B2 | 3/2021 | Foshee et al. |
| 11,179,161 B1 | 11/2021 | Ambro |
| 11,246,600 B1 | 2/2022 | Brown |
| 11,291,459 B2 | 4/2022 | Ramsey et al. |
| 11,304,704 B2 | 4/2022 | Thomas et al. |
| 2001/0049540 A1 | 12/2001 | Santilli |
| 2002/0068946 A1 | 6/2002 | Kortenbach et al. |
| 2002/0111640 A1 | 8/2002 | Krause et al. |
| 2002/0169459 A1 | 11/2002 | Porat |
| 2002/0183785 A1 | 12/2002 | Howell et al. |
| 2003/0074009 A1 | 4/2003 | Ramsey et al. |
| 2003/0236537 A1 | 12/2003 | Hart et al. |
| 2004/0059359 A1 | 3/2004 | Wilson |
| 2004/0112392 A1 | 6/2004 | Parkes |
| 2004/0129277 A1 | 7/2004 | Parkes |
| 2004/0172043 A1 | 9/2004 | Watson et al. |
| 2005/0149069 A1 | 7/2005 | Bertolero et al. |
| 2005/0165421 A1 | 7/2005 | Wilson et al. |
| 2005/0165422 A1* | 7/2005 | Wilson, Jr. |
| 2005/0165423 A1 | 7/2005 | Gallagher et al. |
| 2005/0165424 A1 | 7/2005 | Gallagher et al. |
| 2005/0165429 A1 | 7/2005 | Douglas et al. |
| 2005/0273122 A1 | 12/2005 | Theroux et al. |
| 2005/0277959 A1 | 12/2005 | Cosgrove et al. |
| 2006/0100649 A1 | 5/2006 | Hart |
| 2006/0129170 A1 | 6/2006 | Royce et al. |
| 2006/0200179 A1* | 9/2006 | Barker .................. A61B 17/122 |
| | | 606/157 |
| 2006/0217749 A1 | 9/2006 | Wilson et al. |
| 2007/0016228 A1 | 1/2007 | Salas |
| 2007/0083218 A1 | 4/2007 | Steven |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2007/0173866 A1 | 7/2007 | Sorrentino et al. |
| 2007/0213585 A1 | 9/2007 | Monassevitch et al. |
| 2007/0213747 A1 | 9/2007 | Monassevitch et al. |
| 2007/0276417 A1 | 11/2007 | Mendes et al. |
| 2008/0039879 A1 | 2/2008 | Chin et al. |
| 2008/0045981 A1 | 2/2008 | Margolin et al. |
| 2008/0103512 A1 | 5/2008 | Gately |
| 2008/0208324 A1 | 8/2008 | Glithero et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0171380 A1* | 7/2009 | Whiting ................ A61B 17/122 |
| | | 606/158 |
| 2009/0240266 A1 | 9/2009 | Dennis |
| 2009/0306619 A1 | 12/2009 | Mathias et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274268 A1 | 10/2010 | Singh et al. |
| 2010/0331862 A1 | 12/2010 | Monassevitch et al. |
| 2011/0022079 A1 | 1/2011 | Miles et al. |
| 2011/0112559 A1 | 5/2011 | Monassevitch et al. |
| 2011/0245848 A1 | 10/2011 | Rosenberg et al. |
| 2011/0270285 A1 | 11/2011 | Lissa |
| 2011/0295291 A1 | 12/2011 | Trivisani |
| 2012/0027804 A1 | 2/2012 | Odermatt et al. |
| 2012/0083803 A1 | 4/2012 | Patel et al. |
| 2012/0312858 A1 | 12/2012 | Patankar et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0245653 A1 | 9/2013 | Litherland |
| 2013/0253540 A1 | 9/2013 | Castro et al. |
| 2013/0261642 A1 | 10/2013 | Willett et al. |
| 2014/0018832 A1* | 1/2014 | Shelton, IV |
| 2014/0058411 A1 | 2/2014 | Soutorine et al. |
| 2014/0236170 A1 | 8/2014 | Kethman et al. |
| 2014/0243862 A1* | 8/2014 | Bagaoisan ........... A61B 17/122 |
| | | 606/157 |
| 2015/0066064 A1 | 3/2015 | Kubiak |
| 2015/0127027 A1 | 5/2015 | Vandewalle |
| 2015/0190137 A1 | 7/2015 | Salas |
| 2015/0320426 A1 | 11/2015 | Cosgrove et al. |
| 2016/0151073 A1 | 6/2016 | Castro et al. |
| 2016/0174981 A1 | 6/2016 | Fago et al. |
| 2016/0262756 A1 | 9/2016 | Patankar et al. |
| 2016/0354089 A1 | 12/2016 | Whiting |
| 2017/0009895 A1 | 1/2017 | Stanton et al. |
| 2017/0020530 A1 | 1/2017 | Willett et al. |
| 2017/0027576 A1 | 2/2017 | Castro |
| 2017/0065280 A1 | 3/2017 | Micher et al. |
| 2017/0209151 A1 | 7/2017 | Brown |
| 2017/0311954 A1 | 11/2017 | Brodaczewski et al. |
| 2017/0325818 A1 | 11/2017 | Trivisani |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0221029 A1 | 8/2018 | Menn |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2018/0344321 A1 | 12/2018 | Soutorine et al. |
| 2018/0368852 A1* | 12/2018 | Foshee ................ A61B 17/0487 |
| 2019/0072217 A1 | 3/2019 | Whitaker |
| 2019/0314025 A1 | 10/2019 | Patel et al. |
| 2019/0314026 A1 | 10/2019 | Thomas et al. |
| 2019/0314031 A1* | 10/2019 | Thomas ............... A61B 17/122 |
| 2020/0008810 A1 | 1/2020 | Patel et al. |
| 2020/0046359 A1 | 2/2020 | Thomas et al. |
| 2020/0155158 A1 | 5/2020 | Whiting |
| 2020/0170645 A1 | 6/2020 | Ramsey et al. |
| 2020/0352574 A1 | 11/2020 | Ramsey et al. |
| 2020/0360021 A1 | 11/2020 | Foshee |
| 2020/0405315 A1* | 12/2020 | Zhang .................. A61B 17/122 |
| 2021/0045745 A1 | 2/2021 | Bagaoisan et al. |
| 2021/0128159 A1 | 5/2021 | Taylor et al. |
| 2021/0228212 A1 | 7/2021 | Lebens, III |
| 2021/0267603 A1 | 9/2021 | Foshee et al. |
| 2021/0267604 A1 | 9/2021 | Enniss |
| 2021/0298758 A1 | 9/2021 | Thomas et al. |
| 2021/0346028 A1 | 11/2021 | Brodaczewski et al. |

(56) References Cited

U.S. PATENT DOCUMENTS

| | | |
|---|---|---|
| 2022/0047266 A1 | 2/2022 | Brown |
| 2022/0047269 A1 | 2/2022 | Castro |

FOREIGN PATENT DOCUMENTS

| | | |
|---|---|---|
| CN | 102028517 A | 4/2011 |
| CN | 102860850 A | 1/2013 |
| CN | 103919589 A | 7/2014 |
| CN | 104039247 A | 9/2014 |
| CN | 105054989 A | 11/2015 |
| CN | 105387298 A | 3/2016 |
| CN | 105534558 A | 5/2016 |
| CN | 105682569 A | 6/2016 |
| CN | 106264646 A | 1/2017 |
| EP | 0086640 A2 | 8/1983 |
| EP | 0122046 A1 | 10/1984 |
| EP | 0201344 A2 | 11/1986 |
| EP | 0314064 A2 | 5/1989 |
| EP | 1233705 A2 | 8/2002 |
| EP | 2074954 A1 | 7/2009 |
| EP | 3493747 A1 | 6/2019 |
| EP | 3552561 A2 | 10/2019 |
| GB | 2025511 A | 1/1980 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 58-041541 A | 3/1983 |
| JP | 58-146341 A | 8/1983 |
| JP | 61-259652 A | 11/1986 |
| JP | 03-178648 A | 8/1991 |
| JP | 05-176936 A | 7/1993 |
| JP | 2002-345828 A | 12/2002 |
| JP | 2008-543354 A | 12/2008 |
| JP | 2014-534014 A | 12/2014 |
| KR | 10-1991-0007490 A | 5/1991 |
| KR | 10-2016-0115163 A | 10/2016 |
| WO | 01/35837 A1 | 5/2001 |
| WO | 01/37742 A2 | 5/2001 |
| WO | 2004/043225 A2 | 5/2004 |
| WO | 2006/102578 A1 | 9/2006 |
| WO | 2012/075532 A1 | 6/2012 |
| WO | 2016/094647 A1 | 6/2016 |
| WO | 2016/205343 A1 | 12/2016 |
| WO | 2018/027032 A1 | 2/2018 |
| WO | 2018/196935 A1 | 11/2018 |
| WO | 2018/237277 A1 | 12/2018 |
| WO | 2019/099462 A1 | 5/2019 |
| WO | 2019/169580 A1 | 9/2019 |
| WO | 2020102700 A1 | 5/2020 |

OTHER PUBLICATIONS

International Preliminary Report on Patentability and Written Opinion issued in PCT/US2019/061767, dated May 27, 2021.
International Search Report and Written Opinion issued in PCT/US2019/061767, dated Jan. 13, 2020.

* cited by examiner

SURGICAL CLIP

CROSS-REFERENCE TO RELATED APPLICATIONS

This application claims the benefit of priority to U.S. Provisional Application No. 62/950,819, filed on Dec. 19, 2019, the disclosure of which is hereby incorporated by reference in its entirety.

TECHNICAL FIELD

The present invention relates generally to medical devices, and more particularly, to surgical clips for ligation of tissue.

BACKGROUND

Ligation of tissue (e.g., blood vessels, lymph nodes, nerves, cystic ducts, and cardiac tissue) is a common practice for many surgical procedures. This may be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventors recognize that there is a need to improve one or more features of the surgical clips, such as the tissue-retaining capacity and/or torsional rigidity of the surgical clip. The disclosed devices and methods are directed to mitigating or overcoming one or more of the problems set forth above and/or other problems in the prior art.

One aspect of the present invention is directed to a surgical clip. The surgical clip may include a first leg member having a first inner surface with a curvature, the first leg member having a first thickness in a vertical direction, a first width in a lateral direction, and a first length in a longitudinal direction, where the first width is greater than the first thickness along at least half of the first length. The surgical clip may also include a second leg member having a second inner surface with a curvature, the second leg member having a plurality of teeth.

In some embodiments, the first width is greater than a second width of an inner portion of the first leg member. In some embodiments the first width is greater than a third width of an outer portion of the first leg member. In some embodiments, the first width is defined by at least one lateral protrusion extending from at least one side surface of the first leg member. In some embodiments, the at least one lateral protrusion extends at least half of the first length. In some embodiments, the at least one lateral protrusion extends at least two-thirds of the first length. In some embodiments, the at least one lateral protrusion does not extend the entire first length. In some embodiments, the surgical clip further includes at least one boss member on a distal portion of the first leg member, where a distal end of the at least one lateral protrusion is proximal of the at least one boss member. In some embodiments, the surgical clip further includes a hinge member pivotably joining the first leg member and the second leg member, where a proximal end of the at least one lateral protrusion is distal of the hinge member. In some embodiments, the at least one lateral protrusion includes a first lateral protrusion on a first side surface of the first leg member and a second lateral protrusion on a second side surface of the first leg member. In some embodiments, the plurality of teeth are disposed laterally of the second inner surface, the plurality of teeth being configured to extend past the first inner surface when the surgical clip is in a closed configuration. In some embodiments, the plurality of teeth extend from at least one side surface of the second leg member. In some embodiments, the plurality of teeth includes a first row of teeth and a second row of teeth, and the first row of teeth and the second row of teeth are configured to receive the first inner surface therebetween in a closed configuration. In some embodiments, the first row of teeth and the second row of teeth are staggered longitudinally, the first row of teeth are spaced apart longitudinally and the second row of teeth are spaced apart longitudinally. In some embodiments, the first inner surface and/or the second inner surface is substantially smooth. In some embodiments, the first inner surface has a concave curvature extending from a proximal portion to a distal portion of the first leg member, and the second inner surface has a convex curvature extending from a proximal portion to a distal portion of the second leg member. In some embodiments, the second leg member has a heel at a proximal portion of the second inner surface. In some embodiments, the surgical clip is a one-piece polymeric body. In some embodiments, the surgical clip further includes a hook member on a distal portion of the first leg member; and a tip member on a distal portion of the second leg member, where the hook member is configured to receive the tip member to retain the surgical clip in a closed configuration.

Another aspect of the invention is directed to a surgical clip formed of a one-piece polymeric body. The surgical clip may include a first leg member, a second leg member, and a hinge member. The first leg member may have a first inner surface with a concave curvature, a first outer surface, a first lateral protrusion extending from a first side surface, and a second lateral protrusion extending from a second side surface, the first leg member having a first thickness in a vertical direction defined between the first inner surface and the first outer surface, a first width in a lateral direction defined between the first lateral protrusion and the second lateral protrusion, and a first length in a longitudinal direction, where the first width is greater than the first thickness along at least half of the first length, the first width is greater than a second width of an inner portion of the first leg member, and the first width is greater than a third width of an outer portion of the first leg member. The second leg member may have a second inner surface with a convex curvature, the second leg member having a plurality of teeth disposed laterally of the second inner surface, and the plurality of teeth being configured to extend past the first inner surface when the surgical clip is in a closed configuration. The hinge member may pivotably join the first leg member and the second leg member, where a proximal end of each of the first lateral protrusion and the second lateral protrusion is distal of the hinge member. The surgical clip may include at least one boss member on a distal portion of the first leg member, where a distal end of each of the first lateral protrusion and the second lateral protrusion is proximal of the at least one boss member. The surgical clip may further include a hook member on a distal portion of the first leg member, and a tip member on a distal portion of the second leg member, where the hook member is configured to receive the tip member to retain the surgical clip in the closed configuration.

BRIEF DESCRIPTION OF THE DRAWINGS

In order that the invention may be readily understood, aspects of this invention are illustrated by way of examples in the accompanying drawings.

DETAILED DESCRIPTION

Figure 2:
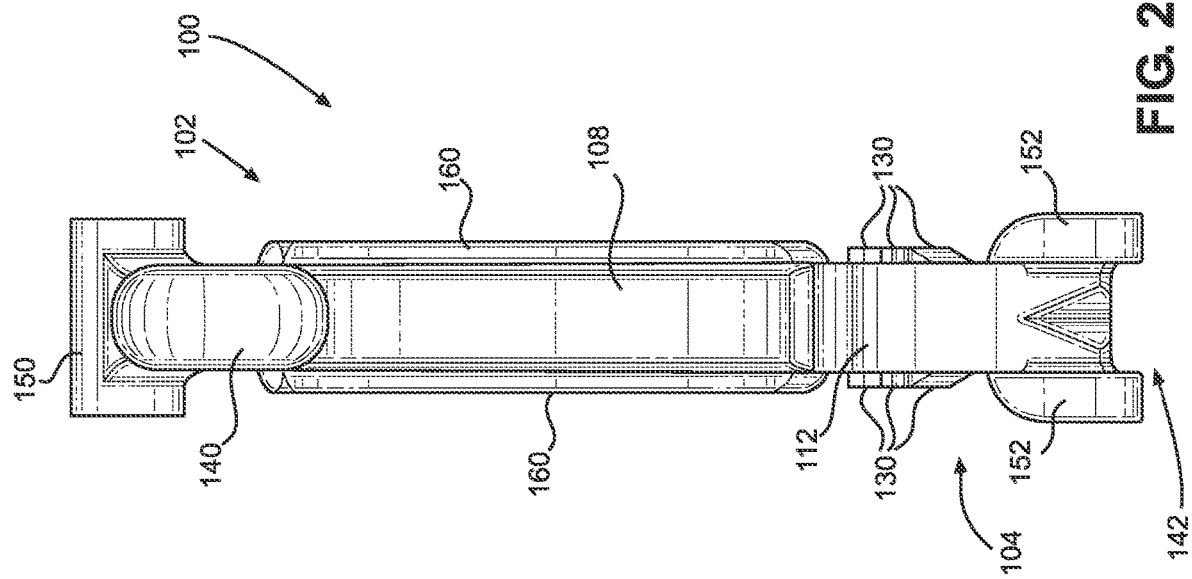
FIG. 2 illustrates an exemplary frontal view of the surgical clip of FIG. 1.

The invention will now be described with reference to the figures, in which like reference numerals may refer to like parts throughout. The present invention is generally directed to a surgical clip configured to compress and/or ligate tissue (e.g., blood vessels, lymph nodes, nerves, cystic tubes, or cardiac tissue). The surgical clip may provide elongated leg members to increase the tissue-retaining capacity. For example, the surgical clip may be sized to fit in a 5 mm clip applier, but have an increased capacity compared to other 5 mm clips. To reinforce and stabilize at least one of the longer leg members, the surgical clip may have at least one lateral protrusion or wing member extending along at least one of the lateral sides of the leg member. The lateral protrusions may provide the leg member with an increased aspect ratio (width/thickness). Thus, the surgical clip is relatively wider along a portion of the thickness to increase the stiffness along at least a portion of the length of the leg member. The surgical clip may also have improved teeth that receive a tissue clamping inner surface therebetween for increased axial security of tissue. The surgical clip may further have features that retain tissue proximate the hinge as the surgical clip closes. The surgical clip may also have rounded leg and/or hinge profiles enhancing applier jaw strength and facilitating easier loading from a cartridge. In some embodiments, the surgical clip may have an improved hinge member. For example, the hinge member may be improved by removing material to form grooves in one or more side surfaces and/or an outer surface to reduce thickness. The grooves may improve the performance of the surgical clip during closure and/or provide features that could be used to help stabilize the surgical clip in the jaws of a clip applier, for example, if the clip applier had mating features.

In accordance with conventional practice, as used herein, and unless otherwise indicated herein, the term "longitudinal" is directed to the dimension which extends along the length of the surgical clip and/or leg members from their respective proximal portions to their respective distal portions, as would be commonly understood by one of skill in the art. Accordingly, the term "length" refers to a dimension of the surgical clip and/or one or more components along its longitudinal direction. Furthermore, the "transverse" direction is directed to any axis or direction which is orthogonal to the longitudinal lengths of the surgical clip or leg members. The term "vertical" refers to a dimension of the surgical clip and/or one or more components along a compression axis of the leg members. The term "thickness" refers to the dimension between opposing edges of the surgical clip and/or one or more components along the compression or vertical direction. The term "width" refers to a dimension of the surgical clip and/or one or more components in a lateral direction substantially transverse to the length and the thickness. The term "concave" and "convex" refers to the curvature of a surface or component visible when viewing an exterior of the surface or component. Similar terminology is used throughout the written disclosure, unless otherwise indicated.

FIGS. 1-5D illustrate a first embodiment of a surgical clip 100 of the present invention. The surgical clip 100 may include a first leg member 102 having a proximal portion and a distal portion, and a second leg member 104 having a proximal portion and a distal portion. The first and second leg members 102, 104 may be integrally joined at the proximal portions by a hinge member 106.

Figure 1:
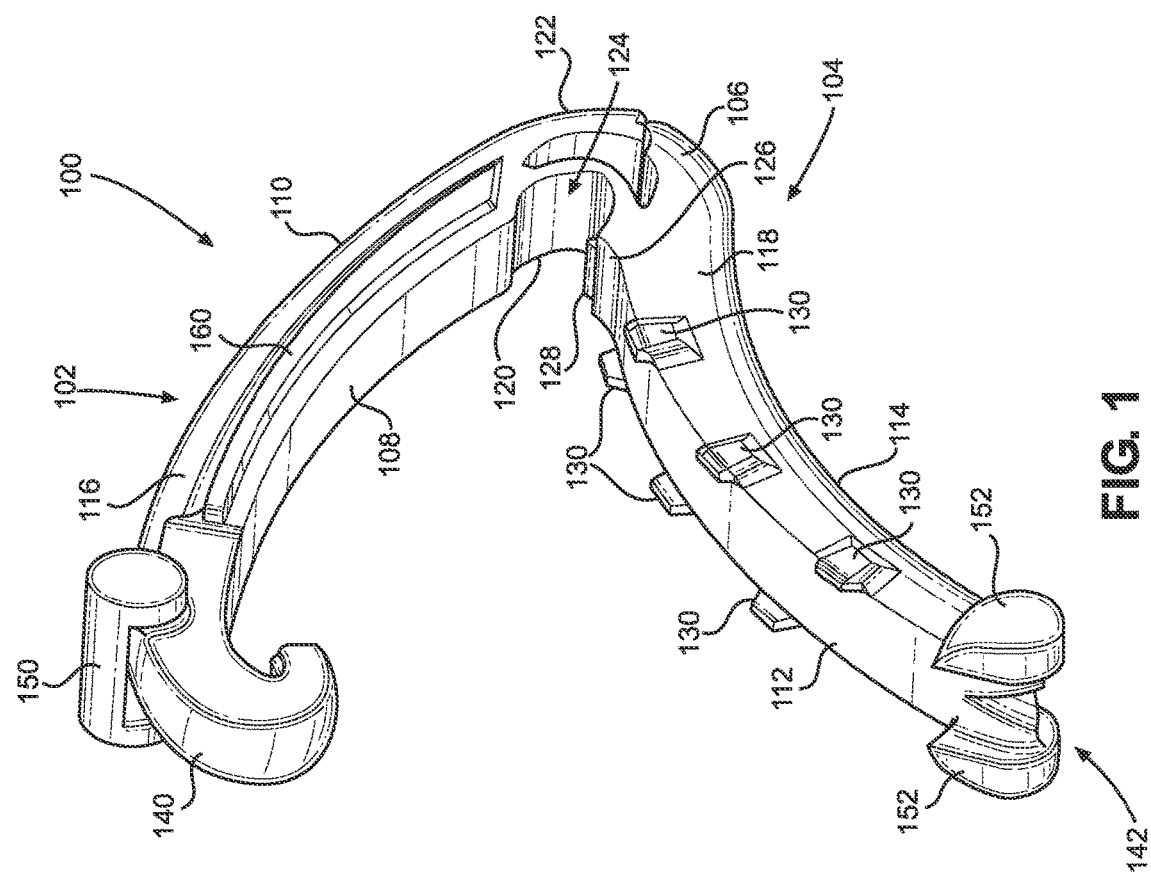
FIG. 1 illustrates an exemplary perspective view of a first exemplary embodiment of a surgical clip in an open configuration according to the present invention.
Figure 4:
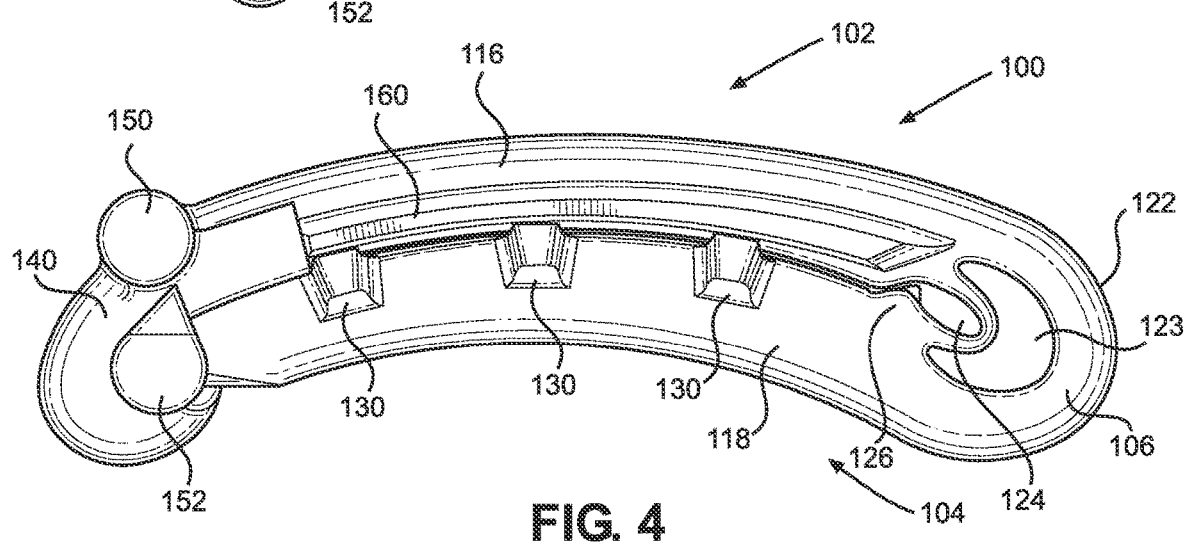
FIG. 4 illustrates an exemplary side view of the surgical clip of FIGS. 1-3 in a closed configuration.

The first and second leg members 102, 104 may be curved along their lengths and include curved surfaces. For example, the first leg member 102 may include a first inner surface 108 and a first outer surface 110, and the second leg member 104 may include a second inner surface 112 and a second outer surface 114. The first inner surface 108 and second outer surface 110 may extend laterally between first side surfaces 116, and the second inner surface 112 and second outer surface 114 may extend laterally between second side surfaces 118. As shown in FIG. 1, the first inner surface 108 may have a concave curvature, and the first outer surface 110 may have a convex curvature, each along the length of the first leg member 102. The second inner surface 112 may have a convex curvature, and the second outer surface 114 may have a concave curvature, each along the length of the second leg member 104. The concave curvature of the first inner surface 108 and/or the convex curvature of the first outer surface 110 may extend from the respective proximal portion to the respective distal portion, substantially the entire length of the first leg member 102. The convex curvature of the second inner surface 112 and/or the concave curvature of the second outer surface 114 may extend from the respective proximal portion to the respective distal portion, substantially the entire length of the second leg member 104. The curvatures of the first leg member 102 and the second leg member 104 may substantially match, and the respective concavity/convexity of the first inner surface 108 and the second inner surface 112 may substantially match. The first and second leg member 102, 104 may bend and/or straighten as the surgical clip 100 closes, and the first and second inner surfaces 108, 112 may be approximated or contact in a closed configuration, as illustrated in FIG. 4. Further discussion of the general curvatures of the leg members 102, 104 and closure of the surgical clip 100 can be found in U.S. Pat. No. 4,834,096, the entire disclosure of which is incorporated herein by reference.

The hinge member 106 may be resiliently flexible and integral to the first and second leg members 102, 104. The hinge member 106 may have a concave inner surface 120 joining the first inner surface 108 and the second inner surface 112 and a convex outer surface 122 joining the first outer surface 110 and the second outer surface 114. The hinge member 106 may define an opening 123 through a thickness between the inner and outer surfaces 120, 122, and the inner surface 120 may define a groove or slot 124 on its inside. The groove 124 may be configured to receive tissue extending between the leg members 102, 104.

Figure 3:
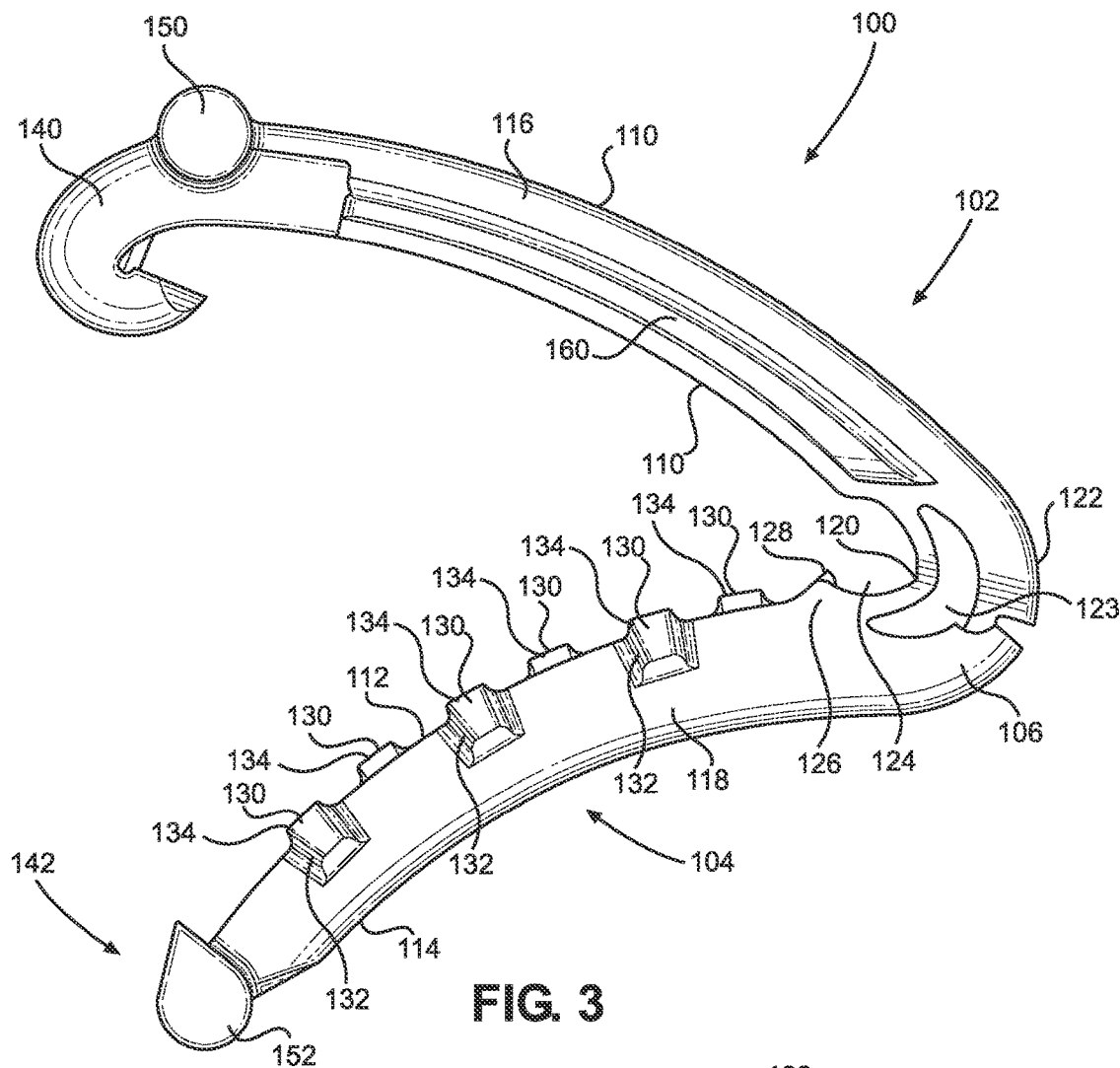
FIG. 3 illustrates an exemplary side view of the surgical clip of FIGS. 1 and 2.

The surgical clip 100 may further have a convex portion or heel 126 on a proximal portion of the second leg member 104 at a distal end of the groove 124. The heel 126 may have a convex curvature having a smaller radius of curvature than the remaining length of the second inner surface 112, providing the heel 126 with increased convexity. The heel 126 may include at least one tooth 128 to increase securement of the tissue in the groove 124. For example, the heel 126 may include a single tooth 128 extending substantially the width of the heel 126. As further illustrated in FIG. 4, the heel 126 and/or at least one tooth 128 may be at least partially received in an opposing portion of the groove 124 in the closed configuration securing the tissue in the groove 124. As illustrated in FIG. 3, the at least one tooth 128 may be angled proximally from the heel 126 toward the hinge member 106 to provide a counterforce to further prevent pull-off of the surgical clip 100.

The surgical clip 100 may also include a latching mechanism having one or more latching elements. For example, the first leg member 102 may transition to a hook member 140 at its distal portion, and the second leg member 104 may transition to a complementary grooved tip member 142 at its distal portion. A distal portion of the hook member 140 may curve inwardly and point generally toward the hinge member 106. The hook member 140 may have one or more transverse beveled surfaces and a concave inner surface which merges with the first inner surface 108 to define a latching recess. The tip member 142 may define a V-shaped groove or slot configured to receive the beveled surfaces of the hook member 140, as the hook member 140 opens or deflects around the tip member 142 and/or the second leg member 104 compresses. The hook member 140 and the tip member 142 may engage to form the latching mechanism. For example, the latching recess may receive the tip member 142 in the course of compressing the surgical clip 100 into the closed configuration (e.g., FIG. 4) when secured position around a vessel or other tissue.

The leg members 102, 104 may include one or more boss members along the length to engage jaws of the clip applier. For example, the first leg member 102 may include one or more boss members 150 protruding perpendicular to opposing side surfaces adjacent to the distal portion of the first leg member 102 and immediately proximal of the hook member 140. In the illustrated example of the surgical clip 100, the one or more boss members 150 may be cylindrical and project outwardly beyond each of the side surfaces 116 of first leg member 102. The boss members 150 may include a bridge section extending the width of the first leg member 102 and joining opposing boss members 150 extending laterally of the side surfaces 116. The second leg member 104 may also include one or more boss members 152 at the distal portion spaced apart by the slot of the tip member 142. The boss members 152 may be cylindrical and protrude perpendicularly to opposing side surfaces 118 of the second leg member 104, extending longitudinally forward beyond the point of tip member 142 and outwardly beyond the side surfaces 118 of second leg member 104. The jaws of the clip applier may engage the boss members 150, 152 and pivot the leg members 102, 104 about the hinge member 106 to compress the surgical clip 100 into the closed and/or latched configuration around a vessel.

As further shown in the embodiment of FIGS. 1-5D, the surgical clip 100 may include a plurality of teeth 130. The teeth 130 may be substantially rigid, such that the teeth 130 do not substantially deflect when engaging tissue. The teeth 130 may be positioned out-board relative to the surgical clip 100. As used herein, the term "out-board" refers to the positioning of the teeth 130 laterally of the inner surface 112. For example, the teeth 130 may be attached to and extend from at least one of the side surfaces 118 and/or substantially perpendicular to the second inner surface 112. The teeth 130 may have a first portion 132 forming a base integrated into the second side surface 118, and a second portion 134 protruding from the second leg member 104 toward the first leg member 102. The first and second portions 132, 134 may be spaced apart from respective first and second portions 132, 134 of adjacent teeth 130. The first portion 132 may be longitudinally wider than the second portion 134 to increase securement of the teeth 130 to the side surfaces 118. The teeth 130 may have a substantially flat outer lateral side surface and a substantially flat inner side surface (defined by the exposed surface of the second portion 134 extending perpendicular from the inner surface 112), as illustrate in FIGS. 5C and 5D. The substantially flat inner side surface of the second portions 134 may make a flush interface or minimal gap with the side surfaces 116 of the first leg member 102. The second portion 134 may further have a substantially flat inner surface extending substantially parallel to the second inner surface 112 to reduce trauma on the ligated tissue.

The teeth 130 may form a first row of teeth 130 integrated into a first side surface 118 and a second row of teeth 130 integrated into a second side surface 118. The teeth 130 may be positioned to clear the first inner surface 108 and extend along the side surfaces 116 of the first leg member 102 to enable the surgical clip 100 to close with minimal or no gap between the inner surfaces 108, 112 ensuring effective closure of small vessels. The first and second rows of teeth 130 may be configured to receive the first inner surface 108 therebetween in the closed configuration, as illustrated in FIG. 4. Thus, in the closed configuration, the teeth 130 may extend from the second side surfaces 118 past the first and second inner surfaces 108, 112, and along or parallel to one of the first side surfaces 116. Thus, in the closed configuration as illustrated in FIG. 4, the teeth 130 may overlap the first and second side surfaces 116, 118 and pass the first and second inner surfaces 108, 112. The teeth 130 may be sufficiently spaced apart from each other along the longitudinal axis of the second leg member 104, thus do not pinch tissue between adjacent teeth 130. The teeth 130 of the first and second rows may be staggered, alternating along the longitudinal axis of the inner surface 112.

The configuration of the teeth 130 may provide a favorable tortuous engagement of tissue with closely approximated tissue engaging surfaces. The larger size of the teeth 130 may improve tissue retention and prevent the tissue from slipping out of the surgical clip. The teeth 130 may further be easy to mold and not interfere with clip appliers. Thus, due to the out-board teeth of the second leg member 104 and the absence of teeth on the first leg member 102, the first inner surface 108 and the second inner surface 112 may be substantially smooth (e.g., substantially without teeth) for substantially the entire length or majority of the length of the first and second leg members 102, 104, with the exception for example of the tooth 128 on the heel 126. For example, as illustrated, the first inner surface 108 may be completely without teeth, and the second inner surface 112 may be without teeth for the majority of its length. Further discussion of features of the out-board teeth 130 can be found in U.S. Patent Publication No. 2018/0368852, the entire disclosure of which is incorporated herein by reference.

The first leg member 102 may have at least one wing member or lateral protrusion 160 extending laterally from one of the first side surfaces 116. For example, the at least one lateral protrusion 160 may include a first lateral protrusion 160 extending from a first side surface 116 and a second lateral protrusion 160 extending from a second side surface 116. The lateral protrusions 160 may reinforce and stabilize the leg member 102 by increasing torsional stiffness. For example, the lateral protrusions 160 may enable the first leg member 102 to be longer without compromising the torsional and/or tissue retention strength of the surgical clip 100. The lateral protrusions 160 may extend longitudinally for at least half of the length of the first leg member 102. In some embodiments, the lateral protrusions 160 may extend longitudinally for at least two-thirds of the length of the first leg member 102. However, the lateral protrusion 160 may not extend the entire length of the first leg member 102. Thus, the lateral protrusions 160 may have a distal end that is proximal of the at least one boss member 150 to prevent interference with the clip applier interface and/or a proximal end that is distal of the hinge member 106 to maintain the flexibility of the hinge member, reducing the pivoting stiffness of the leg members 102, 104. Furthermore, the width of the surgical clip 100 at the lateral protrusions 160 may be narrower than the width of the surgical clip 100 at the boss members 150. As illustrated in the cutaway of the first leg member 102 in FIG. 5A, the protrusion 160 may have an inner surface 164 spaced vertically from the first inner surface 108 and an outer surface 166 spaced vertically from the first outer surface 110. The spacing of the inner surface 164 of the protrusion from the first inner surface 108 may prevent interference with tissue ligation and allow the teeth 130 to receive the inner surface 108 therebetween. The inner surface 164 may be substantially flat and extend substantially perpendicular from the side surface 116 to further reduce any interference with the teeth 130 and/or provide a surface for the teeth 130 to engage in the closed configuration. The outer surface 166 may be angled, tapered, and/or curved (concave or convex) to increase the stability of the protrusion 160 and facilitate manufacturing. As illustrated, the side surface of the protrusion 160 may be free and substantially flat. The spacing of the lateral protrusion 160 from the first inner surface 108 and first outer surface 110 may further optimize the reinforcement of the surgical clip 100.

Figure 5A:
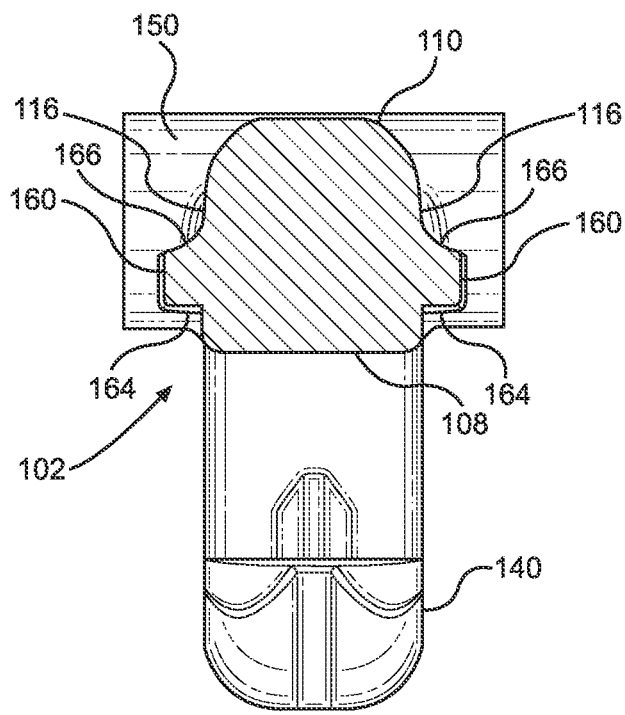
FIG. 5A illustrates an exemplary cut-away view of a first leg member of the surgical clip of FIGS. 1-4.
Figure 5B:
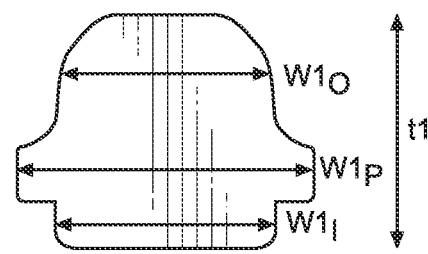
FIG. 5B illustrates an exemplary cross-section of the cut-away view of FIG. 5A.
Figure 5C:
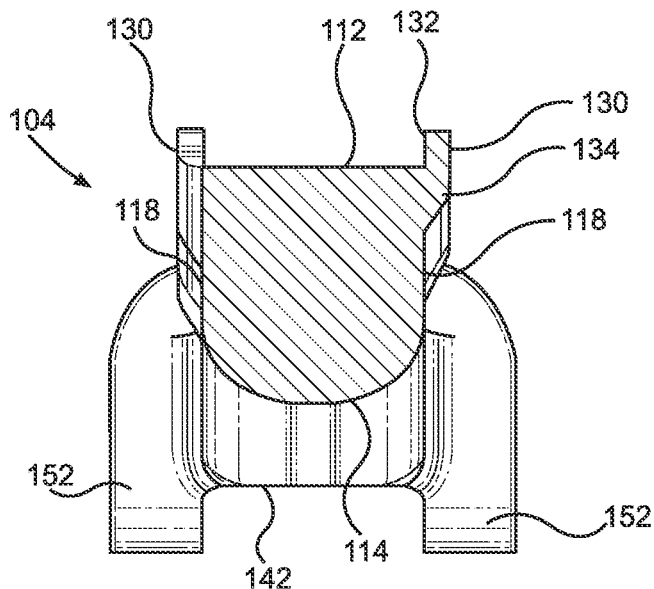
FIG. 5C illustrates an exemplary cut-away view of a second leg member of the surgical clip of FIGS. 1-5B.
Figure 5D:
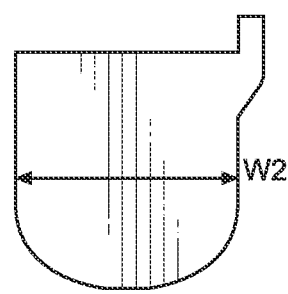
FIG. 5D illustrates an exemplary cross-section of the cutaway view of FIG. 5C.

As further illustrated in the cut-away view of FIG. 5A and the cross-section of FIG. 5B, the first leg member 102 may have a protrusion width ($w1_P$) defined by side surfaces of opposing protrusions 160. The protrusion width ($w1_P$) may be greater than a first inner width ($w1_I$) defined by the dimension between the side surfaces 116 positioned between the protrusions 160 and the first inner surface 108. The protrusion width ($w1_P$) may also be greater than a first outer width ($w1_O$) defined by the dimension between the side surfaces 116 and positioned between the protrusion 160 and to the first outer surface 110. The protrusion width ($w1_P$) may further be greater than a first thickness (t1) defined by the dimension between the first inner surface 108 and the first outer surface 110. The protrusions 160 may extend for at least half of the length of the first leg member 102, thus the protrusion width ($w1_P$) may be greater than the first thickness (t1), first inner width ($w1_I$), and/or the first outer width ($w1_O$) for at least half of the length of the first leg member 102. In embodiments where the protrusions 160 extend for at least two-thirds of the length of the first leg member 102, the protrusion width ($w1_P$) may be greater than the first thickness (t1), first inner width ($w1_I$), and/or the first outer width ($w1_O$) for at least two-third of the length of the first leg member 102. The distal end of the at least one lateral protrusion 160 may define a distal surface that extends substantially perpendicular to the first side surface 116, first inner surface 108 and/or the first outer surface 110. The proximal end of the at least one lateral protrusion 160 may define a proximal surface that extends at an angle proximally relative to the first inner surface 110. The first leg member 102 may have substantially flat side surfaces 116 distal and proximal of the lateral protrusions 160 (between the lateral protrusion 160 and the boss member 152 and/or between the lateral protrusion 160 and the hinge member 106).

Each of the lateral protrusions 160 may themselves have a width from the respective side surface 116 no greater than a quarter of the first inner width ($w1_I$) and the first outer width ($w1_O$). The lateral protrusions 160 may be only on the first leg member 102, thus the second leg member 104 may be without a lateral protrusion. Thus, the protrusion width ($w1_P$) of the first leg member 102 may be greater than a second width (w2) of the second leg member 104 defined by the dimension between the second side surfaces 118, at cross-sections excluding and including the alternating, staggered teeth 130 (although the teeth 130 are not considered part of the side surfaces 118). The lateral protrusions 160 on the first leg member 102 may provide sufficient rigidity to the surgical clip 100 in the closed configuration, and the first leg member 102 having the hook member 140 may require additional rigidity and stability as the surgical clip 100 closes. FIGS. 1-5D illustrate a single lateral protrusion 160 extending from each side surface 116, which facilitates manufacturing of the surgical clip 100. However, it is also contemplated that the surgical clip 100 may include a plurality of lateral protrusions 160 on each side surface 116 (e.g. longitudinally aligned and/or spaced apart) collectively extending the lengths as described herein.

Figure 6:
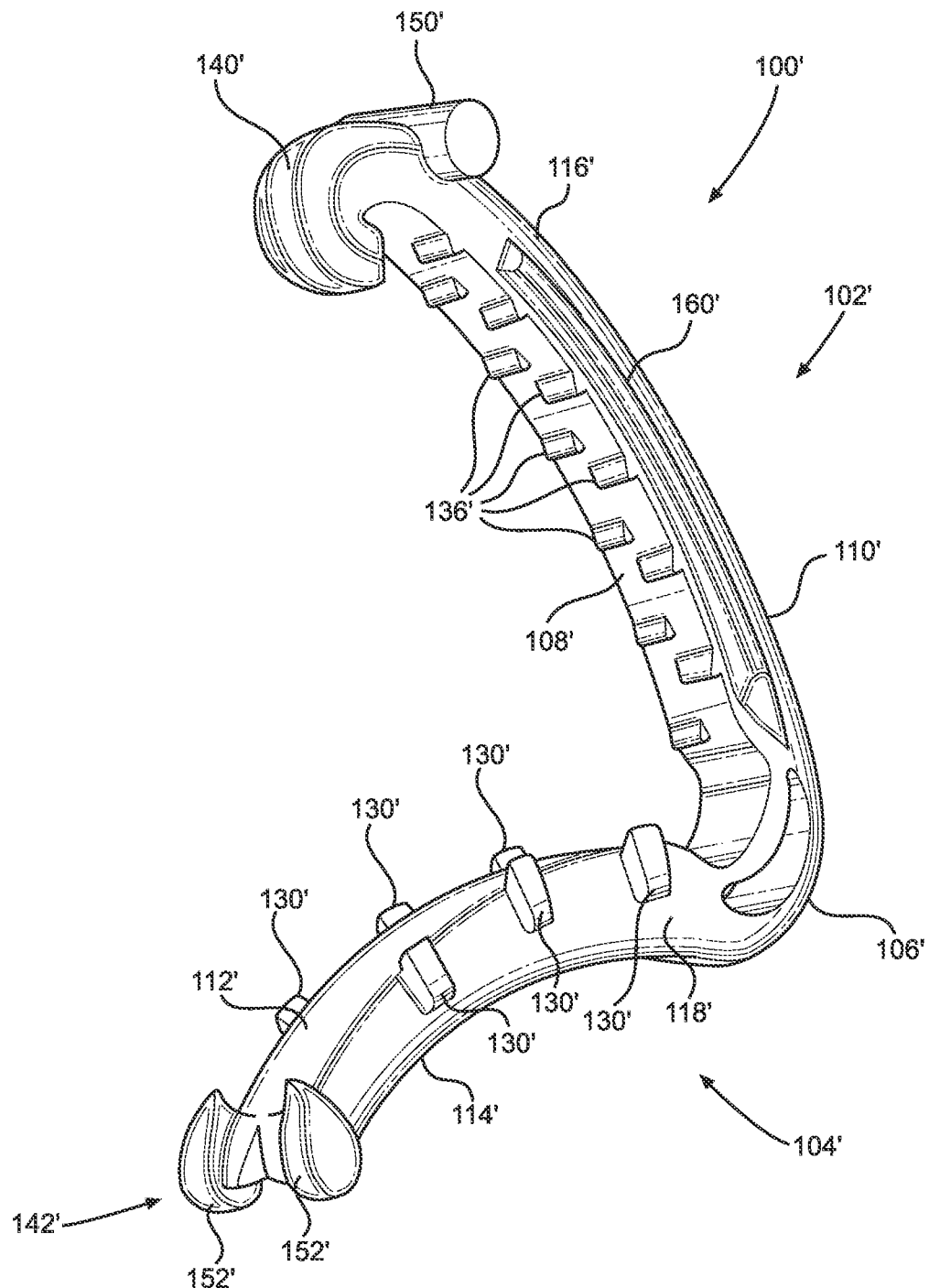
FIG. 6 illustrates an exemplary perspective view of a second exemplary embodiment of a surgical clip in an open configuration.
Figure 8:
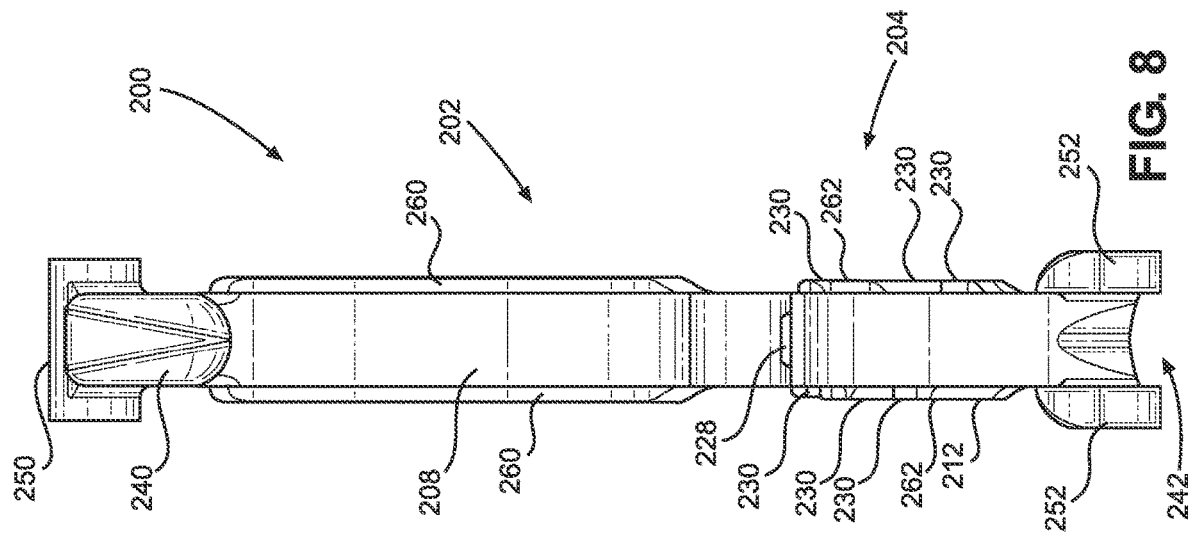
FIG. 8 illustrates an exemplary frontal view of the surgical clip of FIG. 7.

FIG. 6 illustrates a second embodiment of a surgical clip 100' of the present invention. The surgical clip 100' may include a first leg member 102' having a proximal portion and a distal portion, and a second leg member 104' having a proximal portion and a distal portion. The first and second leg members 102', 104' may be integrally joined at the proximal portions by a hinge member 106'. The surgical clip 100' is a modification of the surgical clip 100, thus substantially the entire discussion of FIGS. 1-5D applies to the surgical clip 100' (except when otherwise indicated) and is expressly incorporated herein for brevity sake.

However, the surgical clip 100' differs from the surgical clip 100 in that the surgical clip 100' includes a plurality of teeth 136' on the inner surface 108' of the first leg member 102'. The plurality of teeth 136' may form first and second staggered rows longitudinally along the first inner surface 108'. The plurality of teeth 136' may be angled proximally toward the hinge member 106'. The combination of the teeth 136' extending from the first inner surface 108' and the out-board teeth 130' extending from the second side surfaces 118' may provide favorable retention strength based on the type and mechanical properties of the tissue. The second inner surface 112' may be substantially smooth and engage the teeth 136' of the first inner surface 108'.

FIGS. 7-10D illustrate a third embodiment of a surgical clip 200 of the present invention. The surgical clip 200 may include a first leg member 202 having a proximal portion and a distal portion, and a second leg member 204 having a proximal portion and a distal portion. The first and second leg members 202, 204 may be integrally joined at the proximal portions by a hinge member 206.

Figure 7:
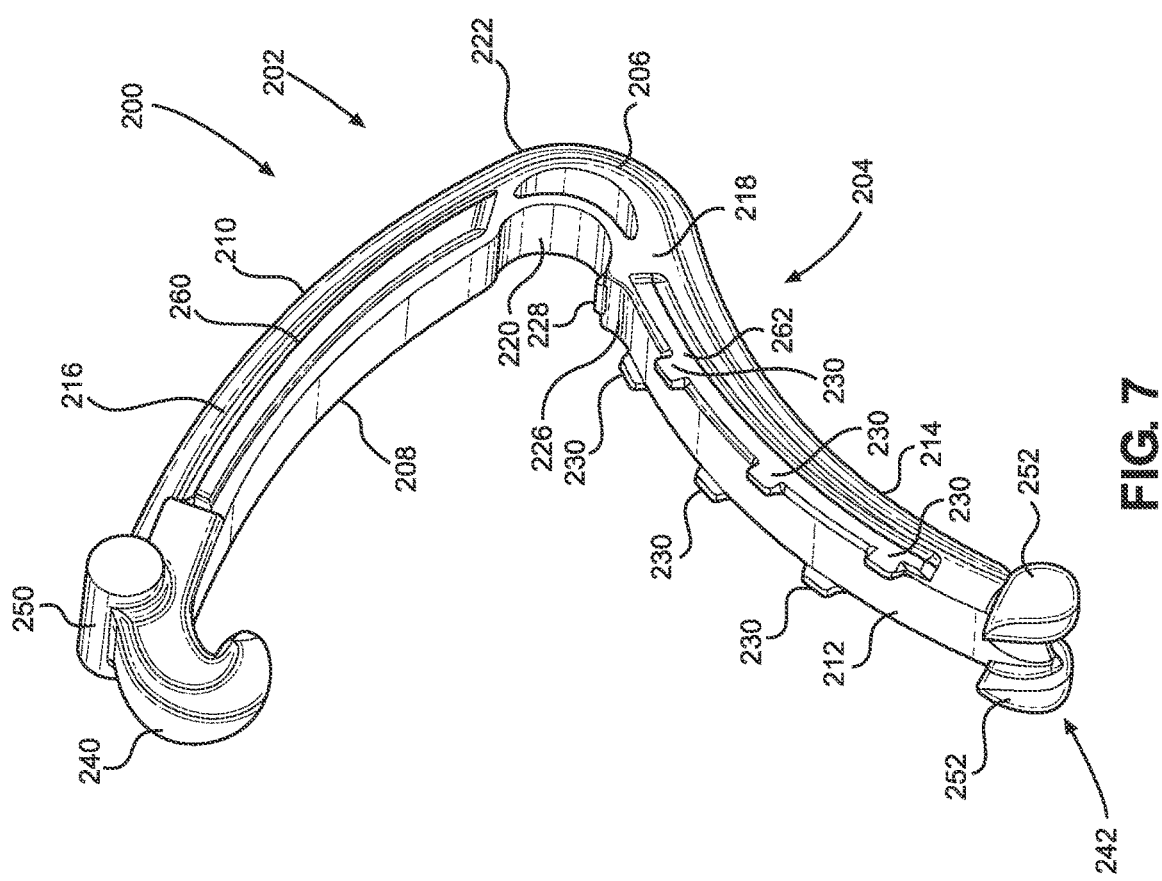
FIG. 7 illustrates an exemplary perspective view of a third exemplary embodiment of a surgical clip in an open configuration.

The first and second leg members 202, 204 may be curved along their lengths and include curved surfaces. For example, the first leg member 202 may include a first inner surface 208 and a first outer surface 210, and the second leg member 204 may include a second inner surface 212 and a second outer surface 214. The first inner surface 208 and second outer surface 210 may extend laterally between first side surfaces 216, and the second inner surface 212 and second outer surface 214 may extend laterally between second side surfaces 218. As shown in FIG. 7, the first inner surface 208 may have a concave curvature, and the first outer surface 210 may have a convex curvature, each along the length of the first leg member 202. The second inner surface 212 may have a convex curvature, and the second outer surface 214 may have a concave curvature, each along the length of the second leg member 204. The concave curvature of the first inner surface 208 and/or the convex curvature of the first outer surface 210 may extend from the respective proximal portion to the respective distal portion, substantially the entire length of the first leg member 202. The convex curvature of the second inner surface 212 and/or the concave curvature of the second outer surface 214 may extend from the respective proximal portion to the respective distal portion, substantially the entire length of the second leg member 204. The curvatures of the first leg member 202 and the second leg member 204 may substantially match, and the respective concavity/convexity of the first inner surface 208 and the second inner surface 212 may substantially match. The first and second leg member 202, 204 may bend and/or straighten as the surgical clip 200 closes, and the first and second inner surfaces 208, 212 may be approximated or contact in a closed configuration, (e.g., as similarly illustrated in FIG. 4). Further discussion of the general curvatures of the leg members 202, 204 and closure of the surgical clip 200 can be found in U.S. Pat. No. 4,834,096, the entire disclosure of which is incorporated herein by reference.

The hinge member 206 may be resiliently flexible and integral to the first and second leg members 202, 204. The hinge member 206 may have a concave inner surface 220 joining the first inner surface 208 and the second inner surface 212 and a convex outer surface 222 joining the first outer surface 210 and the second outer surface 214. The hinge member 206 may define an opening 223 through a thickness between the inner and outer surfaces 220, 222, and the inner surface 220 may define a groove or slot 224 on its inside. The groove 224 may be configured to receive tissue extending between the leg members 202, 204.

Figure 9:
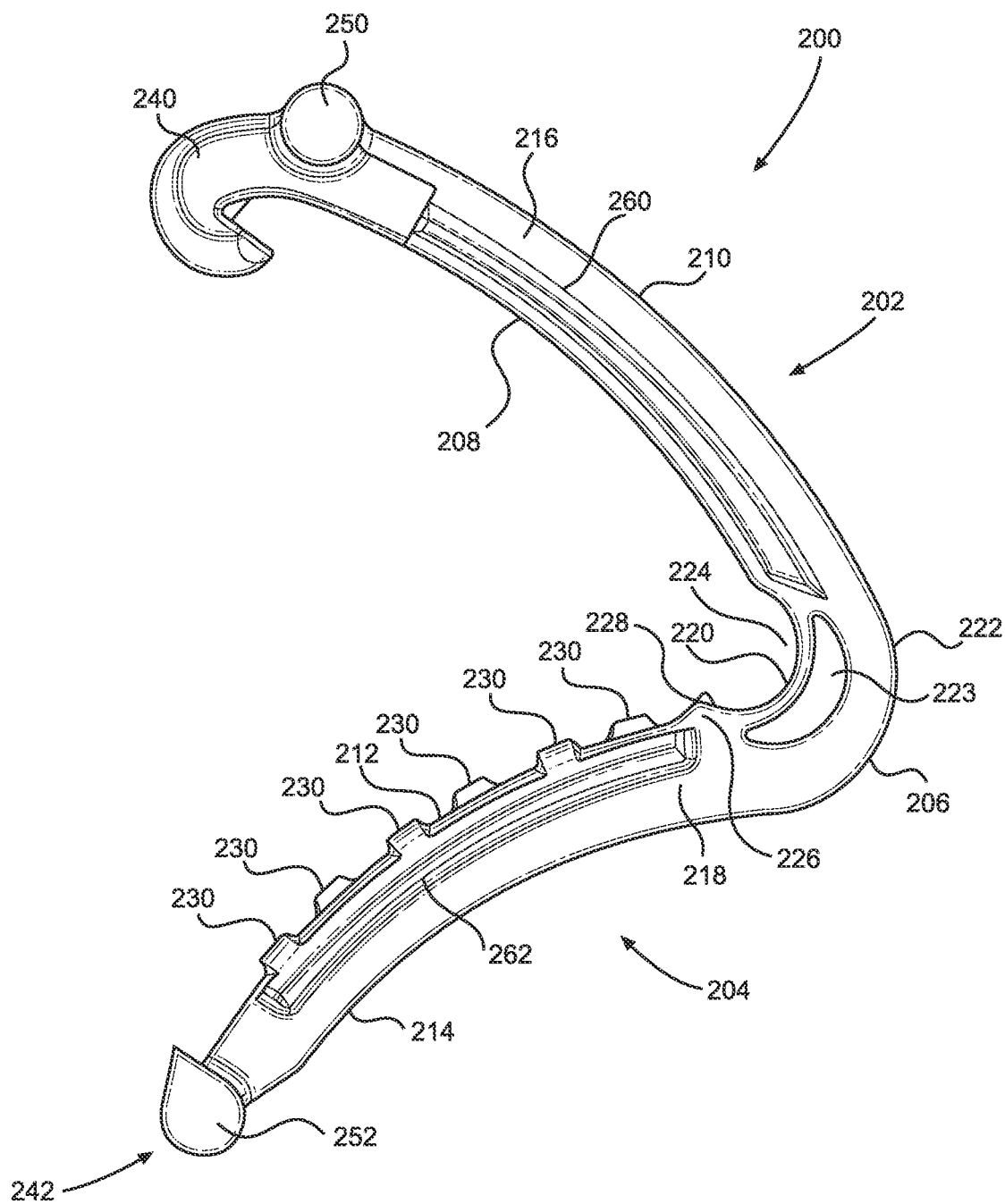
FIG. 9 illustrates an exemplary side view of the surgical clip of FIGS. 7 and 8.

The surgical clip 200 may further have a convex portion or heel 226 on a proximal portion of the second leg member 204 at a distal end of the groove 224. The heel 226 may have a convex curvature having a smaller radius of curvature than the remaining length of the second inner surface 212, providing the heel 226 with increased convexity. The heel 226 may include at least one tooth 228 to increase securement of the tissue in the groove 224. For example, the heel 226 may include a single tooth 228 extending substantially the width of the heel 226. The heel 226 and/or at least one tooth 228 may be at least partially received in an opposing portion of the groove 224 in the closed configuration securing the tissue in the groove 224 (e.g., as similarly illustrated in FIG. 4). As illustrated in FIG. 9, the at least one tooth 228 may be angled proximally from the heel 226 toward the hinge member 206 to provide a counterforce to further prevent pull-off of the surgical clip 200.

The surgical clip 200 may also include a latching mechanism having one or more latching elements. For example, the first leg member 202 may transition to a hook member 240 at its distal portion, and the second leg member 204 may transition to a complementary grooved tip member 242 at its distal portion. A distal portion of the hook member 240 may curve inwardly and point generally toward the hinge member 206. The hook member 240 may have one or more transverse beveled surfaces and a concave inner surface which merges with the first inner surface 208 to define a latching recess. The tip member 242 may define a V-shaped groove or slot configured to receive the beveled surfaces of the hook member 240, as the hook member 240 opens or deflects around the tip member 242 and/or the second leg member 204 compresses. The hook member 240 and the tip member 242 may engage to form the latching mechanism. For example, the latching recess may receive the tip member 242 in the course of compressing the surgical clip 200 into the closed configuration (e.g., as similarly illustrated in FIG. 4) when secured position around a vessel or other tissue.

The leg members 202, 204 may include one or more boss members along the length to engage jaws of the clip applier. For example, the first leg member 202 may include one or more boss members 250 protruding perpendicular to opposing side surfaces adjacent to the distal portion of the first leg member 202 and immediately proximal of the hook member 240. In the illustrated example of the surgical clip 200, the one or more boss members 250 may be cylindrical and project outwardly beyond each of the side surfaces 216 of first leg member 202. The boss members 250 may include a bridge section extending the width of the first leg member 202 and joining opposing boss members 250 extending laterally of the side surfaces 216. The second leg member 204 may also include one or more boss members 252 at the distal portion spaced apart by the slot of the tip member 242. The boss members 252 may be cylindrical and protrude perpendicularly to opposing side surfaces 218 of the second leg member 204, extending longitudinally forward beyond the point of tip member 242 and outwardly beyond the side surfaces 218 of second leg member 204. The jaws of the clip applier may engage the boss members 250, 252 and pivot the leg members 202, 204 about the hinge member 206 to compress the surgical clip 200 into the closed and/or latched configuration around a vessel.

As further shown in the embodiment of FIGS. 7-10D, the surgical clip 200 may include a plurality of teeth 230. The teeth 230 may be substantially rigid, such that the teeth 230 do not substantially deflect when engaging tissue. The teeth 230 may be positioned out-board relative to the surgical clip 200. As used herein, the term "out-board" refers to the positioning of the teeth 230 laterally of the inner surface 212. For example, the teeth 230 may extend inwardly from at least one wing member or lateral protrusion 262 extending perpendicularly from at least one of the side surfaces 218. The teeth 230 may have a substantially flat outer lateral side surface and a substantially flat inner side surface (defined by the exposed surface extending perpendicular from the inner surface 212), as illustrate in FIGS. 10C and 10D. The substantially flat inner side surface of the teeth 230 may make a flush interface or minimal gap with the side surfaces 216 of the first leg member 202. The teeth 230 may further have a substantially flat inner surface extending substantially parallel to the second inner surface 212 to reduce trauma on the ligated tissue.

The teeth 230 may form a first row of teeth 230 extending from a first lateral protrusion 262 integrated into a first side surface 218 and a second row of teeth 230 extending from a second lateral protrusion 262 integrated into a second side surface 218. The teeth 230 may be positioned to clear the first inner surface 208 and extend along the side surfaces 216 of the first leg member 202 to enable the surgical clip 200 to close with minimal or no gap between the inner surfaces 208, 212 ensuring effective closure of small vessels. The first and second rows of teeth 230 may be configured to receive the first inner surface 208 therebetween in the closed configuration (e.g., as similarly illustrated in FIG. 4). Thus, in the closed configuration, the teeth 230 may extend from the lateral protrusions 262 past the first inner surfaces 208, and along or parallel to one of the first side surfaces 216. The teeth 230 may be sufficiently spaced apart from each other along the longitudinal axis of the second leg member 204, thus do not pinch tissue between adjacent teeth 230. The teeth 230 of the first and second rows may be staggered, alternating along the longitudinal axis of the inner surface 212.

The configuration of the teeth 230 may provide a favorable tortuous engagement of tissue with closely approximated tissue engaging surfaces. The larger size of the teeth 230 may improve tissue retention and prevent the tissue from slipping out of the surgical clip. The teeth 230 may further be easy to mold and not interfere with clip appliers. Thus, due to the out-board teeth of the second leg member 204 and the absence of teeth on the first leg member 202, the first inner surface 208 and the second inner surface 212 may be substantially smooth (e.g., substantially without teeth) for substantially the entire length or majority of the length of the first and second leg members 202, 204, with the exception for example of the tooth 228 on the heel 226. For example, as illustrated, the first inner surface 208 may be completely without teeth, and the second inner surface 212 may be without teeth for the majority of its length. Further discussion of features of the out-board teeth 230 can be found in U.S. Patent Publication No. 2018/0368852, the entire disclosure of which is incorporated herein by reference.

The first leg member 202 may have at least one wing member or lateral protrusion 260 extending laterally from one of the first side surfaces 216. For example, the at least one lateral protrusion 260 may include a first lateral protrusion 260 extending from a first side surface 216 and a second lateral protrusion 260 extending from a second side surface 216. The lateral protrusions 260 may reinforce and stabilize the leg member 202 by increasing torsional stiffness. For example, the lateral protrusions 260 may enable the first leg member 202 to be longer without compromising the torsional and/or tissue retention strength of the surgical clip 200. The lateral protrusions 260 may extend longitudinally for at least half of the length of the first leg member 202. In some embodiments, the lateral protrusions 260 may extend longitudinally for at least two-thirds of the length of the first leg member 202. However, the lateral protrusion 260 may not extend the entire length of the first leg member 202. Thus, the lateral protrusions 260 may have a distal end that is proximal of the at least one boss member 250 to prevent interference with the clip applier interface and/or a proximal end that is distal of the hinge member 206 to maintain the flexibility of the hinge member, reducing the pivoting stiffness of the leg members 202, 204. Furthermore, the width of the surgical clip 200 at the lateral protrusions 260 may be narrower than the width of the surgical clip 200 at the boss members 250. As illustrated in the cutaway of the first leg member 202 in FIG. 10A, the protrusion 260 may have an inner surface 264 spaced vertically from the first inner surface 208 and an outer surface 266 spaced vertically from the first outer surface 210. The spacing of the inner surface 264 of the protrusion from the first inner surface 208 may prevent interference with tissue ligation and allow the teeth 230 to receive the inner surface 208 therebetween. The inner surface 264 may be substantially flat and extend substantially perpendicular from the side surface 216 to further reduce any interference with the teeth 230 and/or provide a surface for the teeth 230 to engage in the closed configuration. The outer surface 266 may be angled, tapered, and/or curved (concave or convex) to increase the stability of the protrusion 260 and facilitate manufacturing. As illustrated, the side surface of the protrusion 260 may be free and substantially flat. The spacing of the lateral protrusion 260 from the first inner surface 208 and first outer surface 210 may further optimize the reinforcement of the surgical clip 200.

Figure 10A:
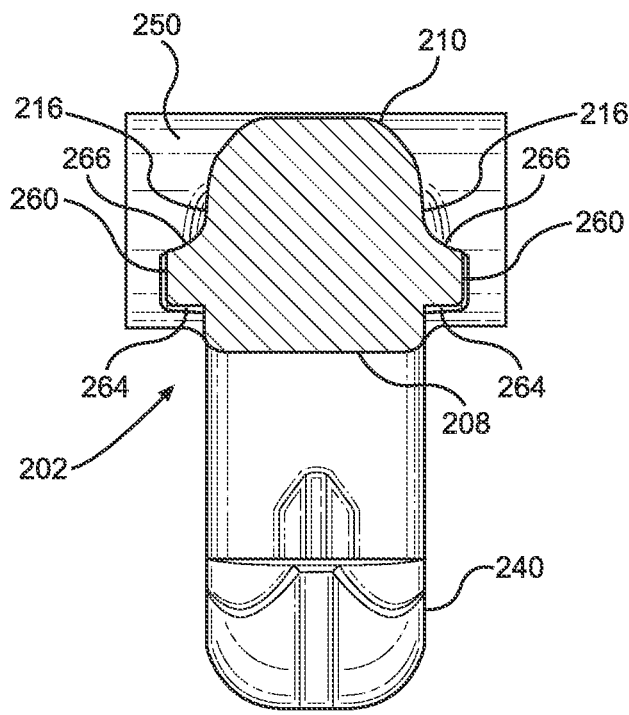
FIG. 10A illustrates an exemplary cutaway view of a first leg member of the surgical clip of FIGS. 7-9.
Figure 10B:
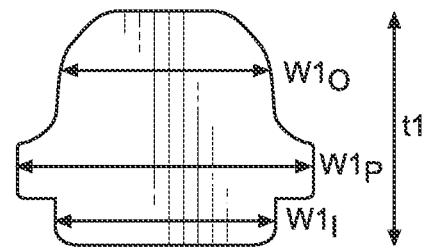
FIG. 10B illustrates an exemplary cross-section of the cutaway view of FIG. 10A.

As further illustrated in the cut-away view of FIG. 10A and the cross-section of FIG. 10B, the first leg member 202 may have a protrusion width ($w1_P$) defined by side surfaces of opposing protrusions 260. The protrusion width ($w1_P$) may be greater than a first inner width ($w1_I$) defined by the dimension between the side surfaces 216 positioned between the protrusion 260 and the first inner surface 208. The protrusion width ($w1_P$) may also be greater than a first outer width ($w1_O$) defined by the dimension between the side surfaces 216 and positioned between the protrusion 260 and to the first outer surface 210. The protrusion width ($w1_P$) may further be greater than a first thickness (t1) defined by the dimension between the first inner surface 208 and the first outer surface 210. The protrusions 260 may extend for at least half of the length of the first leg member 202, thus the protrusion width ($w1_P$) may be greater than the first thickness (t1), first inner width ($w1_I$), and/or the first outer width ($w1_O$) for at least half of the length of the first leg member 202. In embodiments where the protrusion 260 extends for at least two-thirds of the length of the first leg member 202, the protrusion width ($w1_P$) may be greater than the first thickness (t1), first inner width ($w1_I$), and/or the first outer width ($w1_O$) for at least two-third of the length of the first leg member 202. The distal end of the at least one lateral protrusion 260 may define a distal surface that extends substantially perpendicular to the first inner surface 208 and the first outer surface 210. The proximal end of the at least one lateral protrusion 260 may define a proximal surface that extends at an angle proximally relative to the first inner surface 208. The first leg member 202 may have substantially flat side surfaces 216 distal and proximal of the lateral protrusions 260 (e.g., between the lateral protrusion 260 and the boss member 250 and/or between the lateral protrusion 260 and the hinge member 206). The outer surfaces 210, 214 of may have a rounded curvature extending between the respective side surfaces 216, 218 enhancing applier jaw strength and facilitating easier loading from a cartridge. The outer surface 222 of the hinge member 206 may have a similar rounded curvature. Each of the lateral protrusions 260 may themselves have a width from the respective side surface 216 no greater than a quarter of the first inner width ($w1_I$) and the first outer width ($w1_O$). FIGS. 7-10D illustrate a single lateral protrusion 260 extending from each side surface 216, which facilitates manufacturing of the surgical clip 200. However, it is also contemplated that the surgical clip 200 may include a plurality of lateral protrusions 260 on each side surface 216 (e.g. longitudinally aligned and/or spaced apart) collectively extending the lengths as described herein.

Figure 10C:
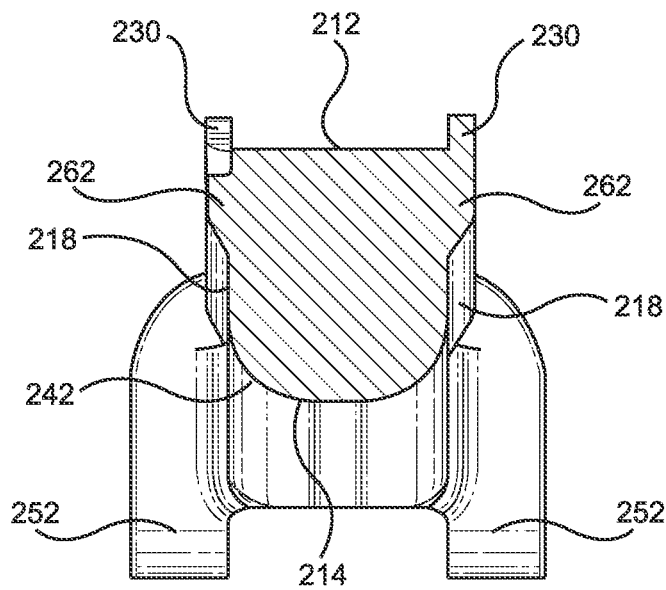
FIG. 10C illustrates an exemplary cutaway view of a second leg member of the surgical clip of FIGS. 7-10B.
Figure 10D:
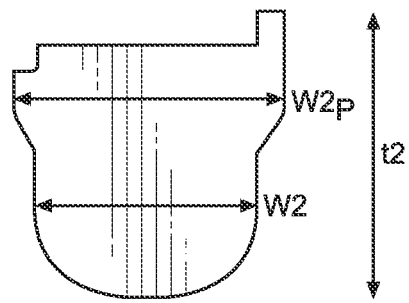
FIG. 10D illustrates an exemplary cross-section of the cutaway view of FIG. 10C.
Figure 11A:
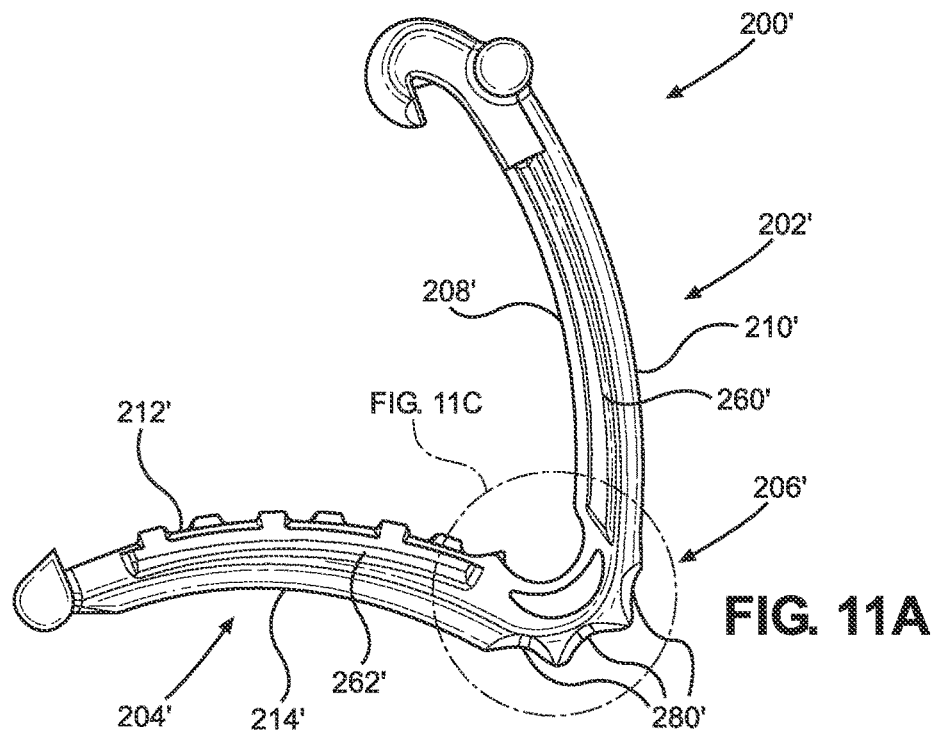
FIGS. 11A-D illustrate a first exemplary embodiment of a grooved hinge member of the surgical clip of FIGS. 7-10D.
Figure 11B:
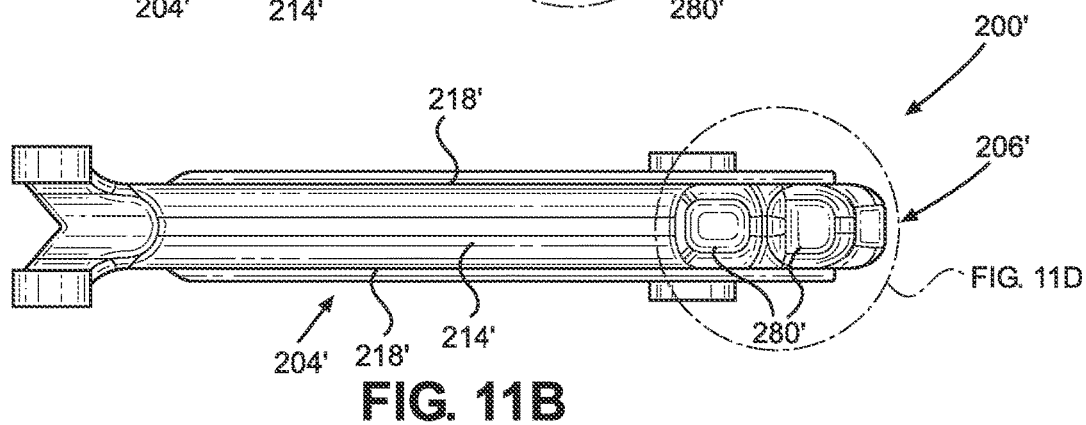
Figure 11C:
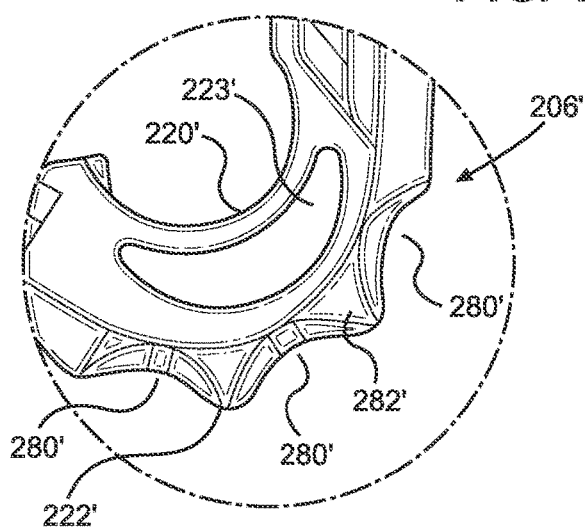
Figure 11D:
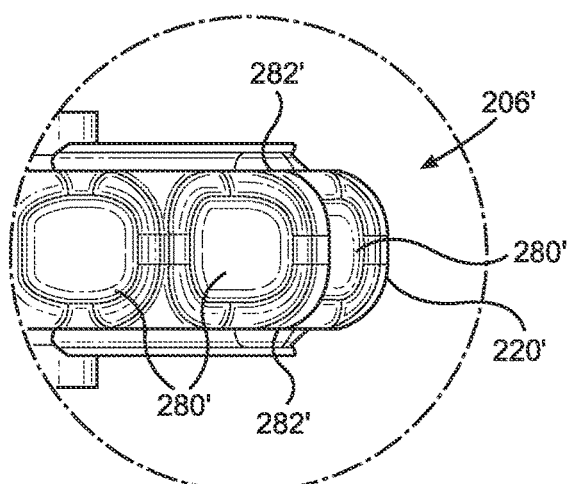
Figure 12A:
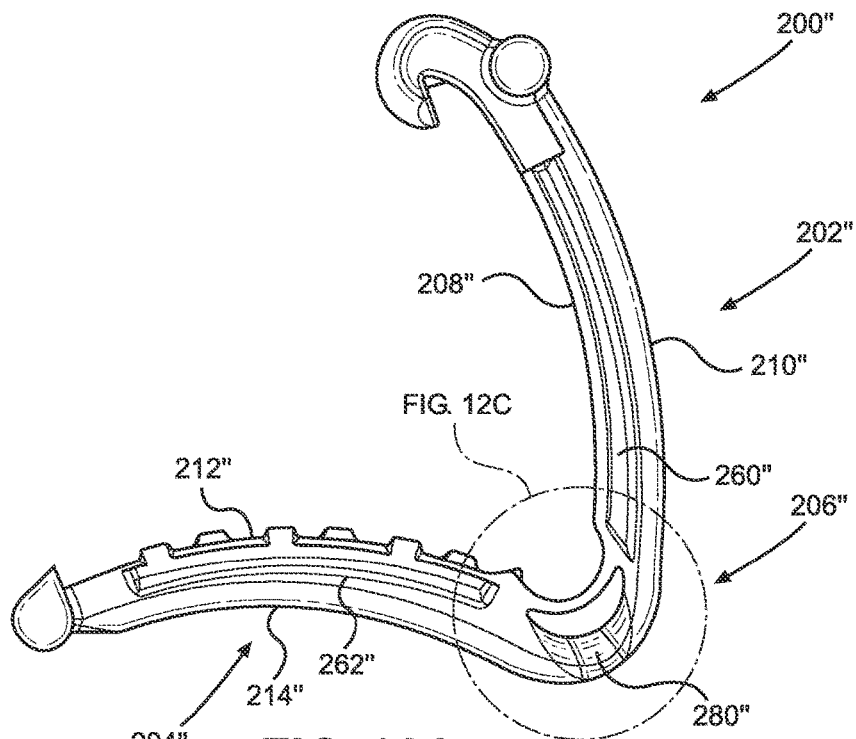
FIGS. 12A-D illustrate a second exemplary embodiment of a grooved hinge member of the surgical clip of FIGS. 7-10D.
Figure 12B:
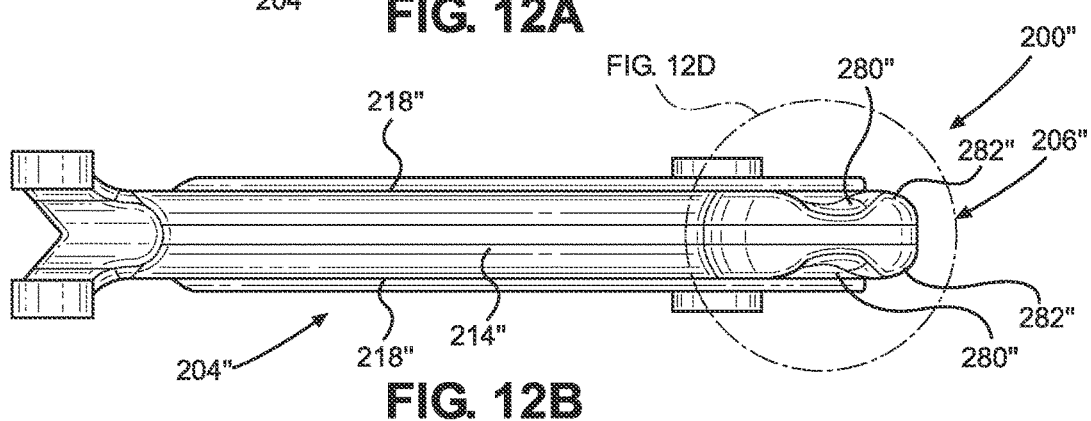
Figure 12C:
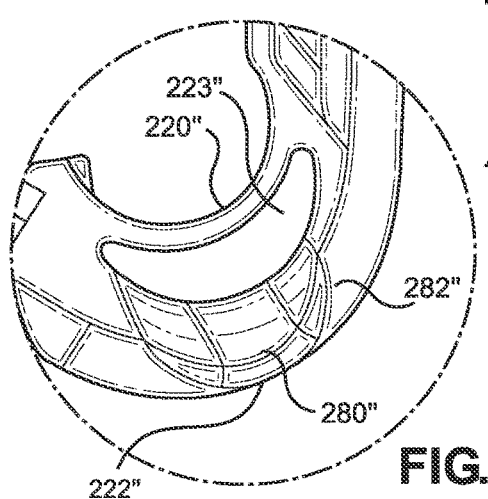
Figure 12D:
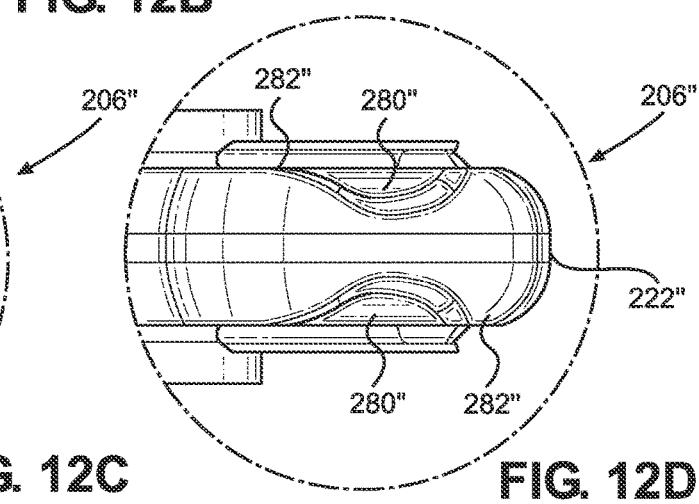

As further illustrated in the cut-away view of FIG. 10C and the cross-section of FIG. 10D, the second leg member 204 may have a protrusion width ($w2_P$) defined by side surfaces of opposing protrusions 262. The protrusion width ($w2_P$) may be greater than a width (w2) defined by the dimension between the side surfaces 218 and positioned between the protrusion 260 and to the second outer surface 214. The protrusion width ($w2_P$) may further be greater than a second thickness (t2) defined by the dimension between the second inner surface 212 and the second outer surface 214. The protrusion 262 may extend for at least half of the length of the second leg member 204, thus the protrusion width ($w2_P$) may be greater than the second thickness (t2), and/or the second width (w2) for at least half of the length of the second leg member 204. In embodiments where the protrusion 262 extends for at least two-thirds of the length of the second leg member 204, the protrusion width ($w2_P$) may be greater than the second thickness (t2), and/or the second width (w2) for at least two-third of the length of the second leg member 204. The distal end of the at least one lateral protrusion 262 may defined a distal surface that extends substantially perpendicular to the first side surface 216, the second inner surface 210, and/or the second outer surface 210. The proximal end of the at least one lateral protrusion 262 may define a proximal surface that extends at an angle proximally relative to the second outer surface 214 and distally relative to the second inner surface 212. The second leg member 204 may have substantially flat side surfaces 218 distal and/or proximal of the lateral protrusions 262 (e.g., between the lateral protrusion 262 and the boss member 252 and/or between the lateral protrusion 262 and the hinge member 206).

FIGS. 11A-D illustrate a fourth embodiment of a surgical clip 200' of the present invention. The surgical clip 200' may include a first leg member 202' having a proximal portion and a distal portion, and a second leg member 204' having a proximal portion and a distal portion. The first and second leg members 202', 204' may be integrally joined at the proximal portions by a hinge member 206'. The surgical clip 200' is a modification of the surgical clip 200, thus substantially the entire discussion of FIGS. 7-10D applies to the surgical clip 200' (except when otherwise indicated) and is expressly incorporated herein for brevity sake. The hinge member 206' may further have one or more grooves 280' in the outer surface 220' extending between the opposing side surfaces 282' of the hinge member 206'. For example, the hinge member 206' may include three grooves, one at the apex of the outer surface 222' and two on opposing sides of the apex. However, in some embodiments, the hinge member 206' may have a single groove 280', for example, at the apex of the outer surface 222'. The grooves 280' may not extend completely through a thickness of the hinge member 206' to the opening 223', such that the grooves 280' are not in communication with the opening 223'. The grooves 280' may be substantially U-shaped and have curved or tapered side portions extending to the side surfaces 282'. The grooves 280' may improve the performance of the surgical clip 200' during closure and/or provide features that may be used to help stabilize the surgical clip 200' in the jaws of a clip applier, for example, if the clip applier had mating features.

FIGS. 12A-D illustrate a fifth embodiment of a surgical clip 200" of the present invention. The surgical clip 200" may include a first leg member 202" having a proximal portion and a distal portion, and a second leg member 204" having a proximal portion and a distal portion. The first and second leg members 202", 204" may be integrally joined at the proximal portions by a hinge member 206". The surgical clip 200" is a modification of the surgical clip 200, thus substantially the entire discussion of FIGS. 7-10D applies to the surgical clip 200" (except when otherwise indicated) and is expressly incorporated herein for brevity sake. The hinge member 206" may further have one or more grooves 280" in one or more of the side surfaces 282". For example, the hinge member 206" may include two grooves, one each in opposing side surfaces 282". As illustrated in the exemplary embodiment, the grooves 280" may extend from the outer surface 222" through the side surfaces 282" and into the opening 223". The grooves 280" may be substantially U-shaped and have curved or tapered side portions. The grooves 280" may improve the performance of the surgical clip 200" during closure and/or provide features that may be used to help stabilize the surgical clip 200" in the jaws of a clip applier, for example, if the clip applier had mating features.

The various embodiments of the surgical clips of the present invention may be made of any suitable size and may be applied to any number of tissues, such as blood vessels, lymph nodes, nerves, cystic ducts, and cardiac tissue. The various embodiments of the surgical clips may be constructed from any suitable biocompatible material, such as metals and polymers. However, the present invention is particularly suitable for practice with polymeric clips. Thus, the various embodiments of the surgical clips 100, 100', 200, 200', 200" preferably consist of a one-piece integral polymeric body formed from injection-molding, extrusion, or otherwise processed from a suitable strong biocompatible engineering plastic. Exemplary materials include homopolymer or co-polymer polyacetal, polyethylene terephthalate (PET), polybutylene terephthalate (PBT), polyoxymethylene, or other thermoplastic materials.

What is claimed is:
1. A surgical clip comprising:
   a first leg member having a first inner surface with a curvature and a pair of first outer side surfaces on opposite sides of the first leg member, the first inner surface extending laterally between the first outer side surfaces, the first leg member having a first thickness in a vertical direction, a first width in a lateral direction, and a first length in a longitudinal direction, wherein the first width is greater than the first thickness along at least half of the first length, and wherein the first width is defined by at least one lateral protrusion extending from at least one of the first outer side surfaces of the first leg member; and a second leg member having a second inner surface with a curvature and a pair of second outer side surfaces on opposite sides of the second leg member, the second inner surface extending laterally between the second outer side surfaces, the second leg member having a plurality of teeth and a second width, wherein the second width is defined by the second outer side surfaces of the second leg member;

wherein the plurality of teeth of the second leg member are configured to extend past the first inner surface of the first leg member when the surgical clip is in a closed configuration, wherein the plurality of teeth of the second leg member are configured to engage an inner surface of the at least one lateral protrusion when the surgical clip is in the closed configuration, and wherein the first width of the first leg member is greater than the second width of the second leg member.

2. The surgical clip of claim 1, wherein the first width is greater than a second width of an inner portion of the first leg member.

3. The surgical clip of claim 1, wherein the first width is greater than a third width of an outer portion of the first leg member.

4. The surgical clip of claim 1, wherein the at least one lateral protrusion extends at least half of the first length.

5. The surgical clip of claim 1, wherein the at least one lateral protrusion extends at least two-thirds of the first length.

6. The surgical clip of claim 1, wherein the at least one lateral protrusion does not extend the entire first length.

7. The surgical clip of claim 6, further comprising at least one boss member on a distal portion of the first leg member, wherein a distal end of the at least one lateral protrusion is proximal of the at least one boss member.

8. The surgical clip of claim 6, further comprising a hinge member pivotably joining the first leg member and the second leg member, wherein a proximal end of the at least one lateral protrusion is distal of the hinge member.

9. The surgical clip of claim 1, wherein the at least one lateral protrusion includes a first lateral protrusion on one of the first outer side surfaces of the first leg member and a second lateral protrusion on another one of the first outer side surfaces of the first leg member.

10. The surgical clip of claim 1, wherein the plurality of teeth are disposed laterally of the second inner surface.

11. The surgical clip of claim 1, wherein the plurality of teeth extend from at least one second outer side surface of the second leg member.

12. The surgical clip of claim 1, wherein the plurality of teeth comprises a first row of teeth and a second row of teeth, and the first row of teeth and the second row of teeth are configured to receive the first inner surface therebetween in a closed configuration.

13. The surgical clip of claim 12, wherein the first row of teeth and the second row of teeth are staggered longitudinally, the first row of teeth are spaced apart longitudinally and the second row of teeth are spaced apart longitudinally.

14. The surgical clip of claim 1, wherein the first inner surface and/or the second inner surface is substantially smooth.

15. The surgical clip of claim 1, wherein the first inner surface has a concave curvature extending from a proximal portion to a distal portion of the first leg member, and the second inner surface has a convex curvature extending from a proximal portion to a distal portion of the second leg member.

16. The surgical clip of claim 1, wherein the second leg member has a heel at a proximal portion of the second inner surface.

17. The surgical clip of claim 1, wherein the surgical clip is a one-piece polymeric body.

18. The surgical clip of claim 1, further comprising:
a hook member on a distal portion of the first leg member; and
a tip member on a distal portion of the second leg member,
wherein the hook member is configured to receive the tip member to retain the surgical clip in a closed configuration.

19. A surgical clip formed of a one-piece polymeric body, the surgical clip comprising:
a first leg member having a first inner surface with a concave curvature, a first outer surface, a first lateral protrusion extending from a first side surface, and a second lateral protrusion extending from a second side surface, the first leg member having a first thickness in a vertical direction defined between the first inner surface and the first outer surface, a first width in a lateral direction defined between the first lateral protrusion and the second lateral protrusion, and a first length in a longitudinal direction, wherein the first width is greater than the first thickness along at least half of the first length, the first width is greater than a second width of an inner portion of the first leg member, and the first width is greater than a third width of an outer portion of the first leg member;
a second leg member having a second inner surface with a convex curvature, the second leg member having a width and a plurality of teeth disposed laterally of the second inner surface, the width defined by opposite outer side surfaces of the second leg member, the plurality of teeth being configured to extend past the first inner surface when the surgical clip is in a closed configuration, and each of the plurality of teeth of the second leg member being configured to engage one of an inner surface of the first lateral protrusion and an inner surface of the second lateral protrusion when the surgical clip is in the closed configuration;
a hinge member pivotably joining the first leg member and the second leg member, wherein a proximal end of each of the first lateral protrusion and the second lateral protrusion is distal of the hinge member;
at least one boss member on a distal portion of the first leg member, wherein a distal end of each of the first lateral protrusion and the second lateral protrusion is proximal of the at least one boss member;
a hook member on a distal portion of the first leg member; and
a tip member on a distal portion of the second leg member,
wherein the hook member is configured to receive the tip member to retain the surgical clip in the closed configuration, and
wherein the first width of the first leg member is greater than the width of the second leg member.

* * * * *